(12) United States Patent
Zopf et al.

(10) Patent No.: US 12,296,097 B2
(45) Date of Patent: May 13, 2025

(54) NASAL AIRWAY DEVICE AND KIT

(71) Applicant: THE REGENTS OF THE UNIVERSITY OF MICHIGAN, Ann Arbor, MI (US)

(72) Inventors: David Adam Zopf, Ann Arbor, MI (US); Allison Powell, Ann Arbor, MI (US); Dian-Ru Li, Ann Arbor, MI (US); Jeffrey Stephen Plott, Algonac, MI (US); Albert J. Shih, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1127 days.

(21) Appl. No.: 17/055,526

(22) PCT Filed: May 16, 2019

(86) PCT No.: PCT/US2019/032586
§ 371 (c)(1),
(2) Date: Nov. 13, 2020

(87) PCT Pub. No.: WO2019/222451
PCT Pub. Date: Nov. 21, 2019

(65) Prior Publication Data
US 2021/0220590 A1    Jul. 22, 2021

Related U.S. Application Data

(60) Provisional application No. 62/672,327, filed on May 16, 2018.

(51) Int. Cl.
*A61M 16/04* (2006.01)
*A61M 16/06* (2006.01)

(52) U.S. Cl.
CPC .... *A61M 16/0461* (2013.01); *A61M 16/0688* (2014.02); *A61M 2205/0216* (2013.01); *A61M 2205/581* (2013.01); *A61M 2205/587* (2013.01)

(58) Field of Classification Search
CPC .......... A61M 16/0461; A61M 16/0688; A61M 2205/0216; A61M 2205/581;
(Continued)

(56) References Cited

U.S. PATENT DOCUMENTS 2,672,138 A * 3/1954 Marion ............... A61M 15/085
128/207.18
3,903,893 A * 9/1975 Scheer ............. A61B 17/12136
604/101.05
(Continued)

FOREIGN PATENT DOCUMENTS

GB        2391812 A *  2/2004  ........ A61M 16/0461
JP   2017079885 A *  5/2017
(Continued)

OTHER PUBLICATIONS

International Search Report and Written Opinion for International Application No. PCT/US19/32586, filed May 16, 2019.

*Primary Examiner* — Tu A Vo
(74) *Attorney, Agent, or Firm* — MARSHALL, GERSTEIN & BORUN LLP

(57) ABSTRACT

An example nasal airway tube includes a tubular body having a distal end and a proximal end. A surface at the distal end including an opening. The tubular body having an overall curvature with a radius of curvature defined relative to a longitudinal axis of the tube. An X-axis is defined by the longitudinal axis of the tube, and a Y-axis extends perpendicularly from the longitudinal axis and has a positive direction defined outwardly relative to the radius of curvature. At least a portion of the opening faces outwardly (Continued)

relative to the radius of curvature. A vector normal to a plane defined by the opening includes a positive Y-coordinate.

18 Claims, 44 Drawing Sheets

(58) Field of Classification Search
CPC ........ A61M 2205/587; A61M 16/0666; A61M 16/0677; A61M 16/0672
See application file for complete search history.

(56) References Cited

U.S. PATENT DOCUMENTS

| | | | | |
|---|---|---|---|---|
| 4,736,741 | A * | 4/1988 | Payton | A61M 16/0666 |
| | | | | 128/207.18 |
| 4,821,715 | A * | 4/1989 | Downing | A61M 16/0461 |
| | | | | 128/207.18 |
| 4,852,564 | A * | 8/1989 | Sheridan | A61M 16/08 |
| | | | | 138/119 |
| 5,024,220 | A * | 6/1991 | Holmgreen | A61M 16/0463 |
| | | | | 128/207.14 |
| 5,097,827 | A * | 3/1992 | Izumi | A61M 25/02 |
| | | | | 128/911 |
| 5,185,005 | A * | 2/1993 | Ballantyne | A61M 25/02 |
| | | | | 604/179 |
| 5,556,385 | A * | 9/1996 | Andersen | A61J 15/0042 |
| | | | | 604/174 |
| 5,562,078 | A * | 10/1996 | Dzwonkiewicz | A61B 7/023 |
| | | | | 128/207.14 |
| 5,692,506 | A * | 12/1997 | Linder | A61M 25/0068 |
| | | | | 607/124 |
| D390,656 | S * | 2/1998 | Linder | D24/112 |
| 6,098,617 | A * | 8/2000 | Connell | A61M 16/0486 |
| | | | | 128/207.14 |
| 6,394,093 | B1 * | 5/2002 | Lethi | A61M 16/0461 |
| | | | | 128/207.14 |
| 6,488,664 | B1 * | 12/2002 | Solomon | F16L 33/035 |
| | | | | 602/17 |
| 7,604,627 | B2 * | 10/2009 | Kojouri | A61J 15/0003 |
| | | | | 604/516 |
| 2001/0035185 | A1 * | 11/2001 | Christopher | A61M 16/0683 |
| | | | | 128/200.24 |
| 2005/0081861 | A1 | 4/2005 | Nasir | |
| 2005/0236001 | A1 * | 10/2005 | Williams | A61M 25/02 |
| | | | | 128/207.18 |
| 2006/0048775 | A1 * | 3/2006 | Dunlap | A61M 16/0461 |
| | | | | 128/207.18 |
| 2006/0282086 | A1 * | 12/2006 | Abdelatti | A61M 16/0461 |
| | | | | 606/108 |
| 2006/0283464 | A1 * | 12/2006 | Dunlap | A61M 16/0461 |
| | | | | 128/206.28 |
| 2008/0078407 | A1 * | 4/2008 | Sherman | A61M 16/0461 |
| | | | | 128/207.18 |
| 2009/0248057 | A1 * | 10/2009 | Kotler | A61F 5/08 |
| | | | | 128/207.18 |
| 2010/0224186 | A1 * | 9/2010 | Uesugi | A61M 16/0459 |
| | | | | 128/207.14 |
| 2010/0242967 | A1 * | 9/2010 | Burbank | A61F 5/56 |
| | | | | 128/207.18 |
| 2012/0010646 | A1 * | 1/2012 | Keith | A61B 17/3421 |
| | | | | 606/196 |
| 2012/0080037 | A1 * | 4/2012 | Guyuron | A61M 16/0431 |
| | | | | 128/207.18 |
| 2012/0118297 | A1 * | 5/2012 | Barodka | A61M 16/0445 |
| | | | | 128/848 |
| 2013/0019872 | A1 * | 1/2013 | Guyuron | A61M 16/0427 |
| | | | | 128/207.18 |
| 2013/0152940 | A1 * | 6/2013 | Larson | A61M 16/0461 |
| | | | | 128/207.18 |
| 2013/0338521 | A1 * | 12/2013 | Thompson | A61M 16/085 |
| | | | | 604/179 |
| 2014/0332009 | A1 * | 11/2014 | Haider | A61M 16/0497 |
| | | | | 128/207.14 |
| 2016/0235933 | A1 | 8/2016 | Garrett et al. | |

FOREIGN PATENT DOCUMENTS

| | | | |
|---|---|---|---|
| JP | 2017093477 A * | 6/2017 | |
| WO | WO-0013575 A1 * | 3/2000 | ........... A61B 5/0088 |

* cited by examiner

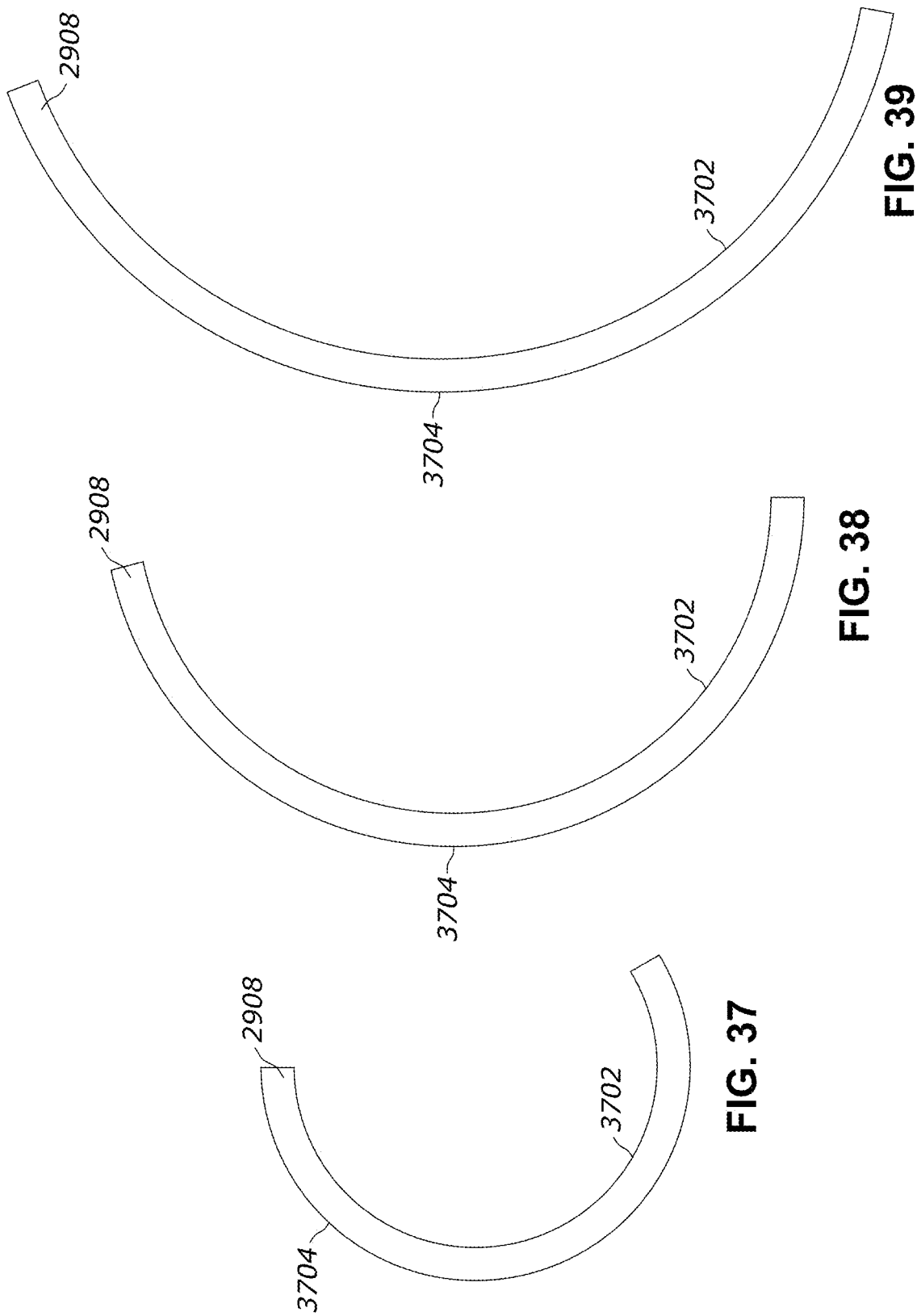

NASAL AIRWAY DEVICE AND KIT

CROSS-REFERENCE TO RELATED APPLICATION

This present application is the US national phase of International Patent Application No. PCT/US2019/032586, filed May 16, 2019, which claims priority to U.S. Provisional Patent Application No. 62/672,327, filed May 16, 2018. The priority application, U.S. 62/672,327, is hereby incorporated by reference in its entirety.

FIELD OF THE DISCLOSURE

This application relates generally to a nasal airway device and more, specifically, to a nasal airway device including an attachment mechanism that enables long-term airway management. A nasal airway device kit including a nasal airway device and a stylet is also disclosed.

BACKGROUND

Current attachment mechanisms for tubes placed into the airway use significant adhesive and tape or wrap around the head. Long term nasal airway devices in the form of nasopharyngeal airway devices frequently employ a rudimentary attachment consisting of an industrial safety pin, tape, and string to maintain location of the tubing. Such a rather crude attachment must be recreated on a weekly or even daily basis by a caregiver. The strong adhesives currently used typically lead to significant irritation and facial tissue damage. Other products, such as the nasal trumpet, are only suitable for acute use. There is currently no approved device for long-term nasopharyngeal airway management. Because long term nasal airway devices are not available, more aggressive procedural interventions to maintain airway patency are required such as intubation, tracheostomy, and mandibular distraction surgery. Furthermore, nasopharyngeal airway devices can be difficult to insert into the patient and may lead to patient discomfort and even bleeding within the nose.

SUMMARY

In accordance with a first example, a nasal airway tube includes a tubular body having a distal end and a proximal end. A surface at the distal end including an opening. The tubular body having an overall curvature with a radius of curvature defined relative to a longitudinal axis of the tube. An X-axis is defined by the longitudinal axis of the tube, and a Y-axis extends perpendicularly from the longitudinal axis and has a positive direction defined outwardly relative to the radius of curvature. At least a portion of the opening faces outwardly relative to the radius of curvature. A vector normal to a plane defined by the opening includes a positive Y-coordinate.

In accordance with a second example, a nasal airway tube includes a tubular body having a distal end and a proximal end. A surface at the distal end includes an opening. The tubular body having an overall curvature with a radius of curvature defined relative to a longitudinal axis of the tube. A principal axis is defined by the longitudinal axis of the tube, and a secondary axis extends perpendicularly from the longitudinal axis. An angle defined between the secondary axis and a vector normal to a plane defined by the opening is between about 0° and about 45°.

In accordance with a third example, a nasal airway tube includes a tubular body having a distal end and a proximal end. A surface at the distal end that includes an opening defined by an annulus includes a leading end and a trailing end. A first plane bisects an apex of the tube and a longitudinal axis of the tube. A second plane substantially bisects the leading end and the trailing end of the opening. An angle defined between the first plane and the second plane is between about 0° and about 45°.

In accordance with a fourth example, a nasal airway tube includes a distal end and a proximal end. An end surface at the distal end defines an opening including a leading end and a trailing end. The leading end being closest, relative to the trailing end, to a lowest most point of the opening and the trailing end being closest, relative to the leading end, to a highest most point of the opening. The leading end being spaced a greater distance from an apex of the tube when the tube is being inserted into a nostril of a patient.

In accordance with a fifth example, a nasal airway device includes a tube having a distal end and a proximal end. The nasal airway device also includes an attachment mechanism coupled to the proximal end of the tube. The attachment mechanism including a tube access channel, a plurality of fins on an exterior surface of the tube access channel, at least one of the plurality of fins being deformable, and a bridge connected at a proximal portion of the exterior surface of the tube access channel.

In accordance with a sixth example, a nasal airway device kit includes a nasal airway device including a tube having a distal end, a proximal end, an external diameter, and an internal diameter. The nasal airway device kit includes an attachment mechanism coupled to the proximal end of the tube. The attachment mechanism including a tube access channel having an interior diameter that is greater than the external diameter of the tube or can expand to accommodate the external diameter of the tube. A plurality of fins on an exterior surface of the tube access channel. At least one of the plurality of fins being deformable, and a bridge connected at a proximal portion of the exterior surface of the tube access channel. The nasal airway device kit also includes a stylet having an outer diameter less than the internal diameter of the tube.

In further accordance with the foregoing first, second, third, fourth, fifth, and/or sixth examples, an apparatus and/or method may further include any one or more of the following:

In accordance with one example, the leading end being closest, relative to the trailing end, to a lowest most point of the opening and the trailing end being closest, relative to the leading end, to a highest most point of the opening. The leading end being spaced a greater distance from an apex of the tube when the tube is being inserted into a nostril of a patient.

In accordance with another example, an angle defined between the Y-axis and the vector normal to the plane defined by the opening is between about 0° and about 45°.

In accordance with another example, the opening includes a leading end and a trailing end, and a first plane bisects an apex of the tube and the leading end and the trailing end of the opening.

In accordance with another example, the opening includes a leading end and a trailing end. A first plane bisects an apex of the tube and a second plane bisects the leading end and the trailing end. An angle defined between the first plane and the second plane is between about 0° and about 45°.

In accordance with another example, an angle between the vector and the Y-axis is between about 0° and about positive 45° to adapt the nasal airway tube to be inserted into a left nostril of a patient.

In accordance with another example, an angle between the vector and the Y-axis is between about 0° and about negative 45° to adapt the nasal airway tube to be inserted into a right nostril of a patient.

In accordance with another example, an angle between a tangent of a leading edge of the tube and the plane defined by the opening is between about 20° and about 50°.

In accordance with another example, further including a side opening defined by the tube.

In accordance with another example, the side opening is oval shaped.

In accordance with another example, the tube has a radius of curvature of between about 0.010 millimeters $(mm)^{-1}$ and about 0.04 $mm^{-1}$.

In accordance with another example, a lower surface of the tube adjacent the opening includes a protrusion.

In accordance with another example, the surface at the distal end includes a convex surface.

In accordance with another example, along an axis of the tube between a trailing end and a leading end of the opening, respective sides of the opening include associated convex portions and associated concave portions.

In accordance with another example, along the longitudinal axis of the tube, the tube includes convex portions and concave portions.

In accordance with another example, the opening includes a leading end and a trailing end and the tube includes an outward-facing surface and an inward-facing surface, the outward-facing surface terminating at the trailing end and the inward-facing surface terminating at the leading end.

In accordance with another example, further including a plurality of side openings defined by the inward-facing surface.

In accordance with another example, further including a plurality of side openings defined by the outward-facing surface.

In accordance with another example, further including an attachment mechanism coupled to the proximal end of the tube. The attachment mechanism adapted to be inserted into the nostril of a patient.

In accordance with another example, the leading end being approximately a lowest most point of the opening and the trailing end being approximately a highest most point of the opening.

In accordance with another example, the attachment mechanism includes at least one of medical grade silicone elastomer and thermoplastic elastomer.

In accordance with another example, the bridge includes a ductile material that holds a shape once deformed.

In accordance with another example, the fins are straight, curved, or a combination thereof.

In accordance with another example, the fins are semi-occluding.

In accordance with another example, the fins are spaced around a circumference of the exterior surface of the tube access channel by one or more angles, or at least one of the fins includes a cutout.

In accordance with another example, at least one of the plurality of fins at least one of: connects to the exterior surface of the tube access channel at a connection end and has a free end that protrudes out from the exterior surface of the tube access channel at an angle ranging from 0 to 180 degrees; connects to the exterior surface of the tube access channel at a first end and a second end; connects to a sliding member at the first end and to the exterior surface of the tube access channel at the second end; and connects to the exterior surface of the tube access channel so as to create an enclosed volume between the exterior surface of the tube access channel and the fin.

In accordance with another example, the fins are adjustable via at least one of air pressure, fluid pressure, and mechanical supports.

In accordance with another example, the fins include at least one of an adhesive to improve securement, surface texture, thermal expanding members that grow in the presence of heat, and moisture-sensitive expanding members that grow in the presence of moisture.

In accordance with another example, the bridge extends in a first direction away from the exterior surface of the tube access channel.

In accordance with another example, the bridge extends both in a first direction and in a second direction away from the exterior surface of the tube access channel.

In accordance with another example, the bridge includes a hook that curves or projects toward a distal end of the attachment mechanism.

In accordance with another example, the hook includes secondary fins.

In accordance with another example, the tube access channel is a first tube access channel, and the bridge connects the first tube access channel to a second tube access channel.

In accordance with another example, the second tube access channel has a plurality of fins on an outer surface of the second tube access channel, at least one of the plurality of fins on the outer surface of the second tube access channel being deformable.

In accordance with another example, at least one of the stylet and the tube have a rounded or tapered tip to facilitate insertion into a nose.

In accordance with another example, the stylet includes a thermoplastic material with low surface friction.

In accordance with another example, the stylet includes a placement aid.

In accordance with another example, the tube at least one of: has hybrid or heterogeneous material properties with locally variable stiffness; and includes medical grade PVC, silicone, or another semi-rigid thermoplastic.

In accordance with another example, the external diameter of the tube is between 2 and 6 mm.

BRIEF DESCRIPTION OF THE DRAWINGS

While the specification concludes with claims particularly pointing out and distinctly claiming the subject matter that is regarded as the present disclosure, it is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIG. 37 illustrates the tube of FIG. 29A having a first radius of curvature;

FIG. 38 illustrates the tube of FIG. 29A having a second radius of curvature;

FIG. 39 illustrates the tube of FIG. 29A having a third radius of curvature;

DETAILED DESCRIPTION

Figure 1:
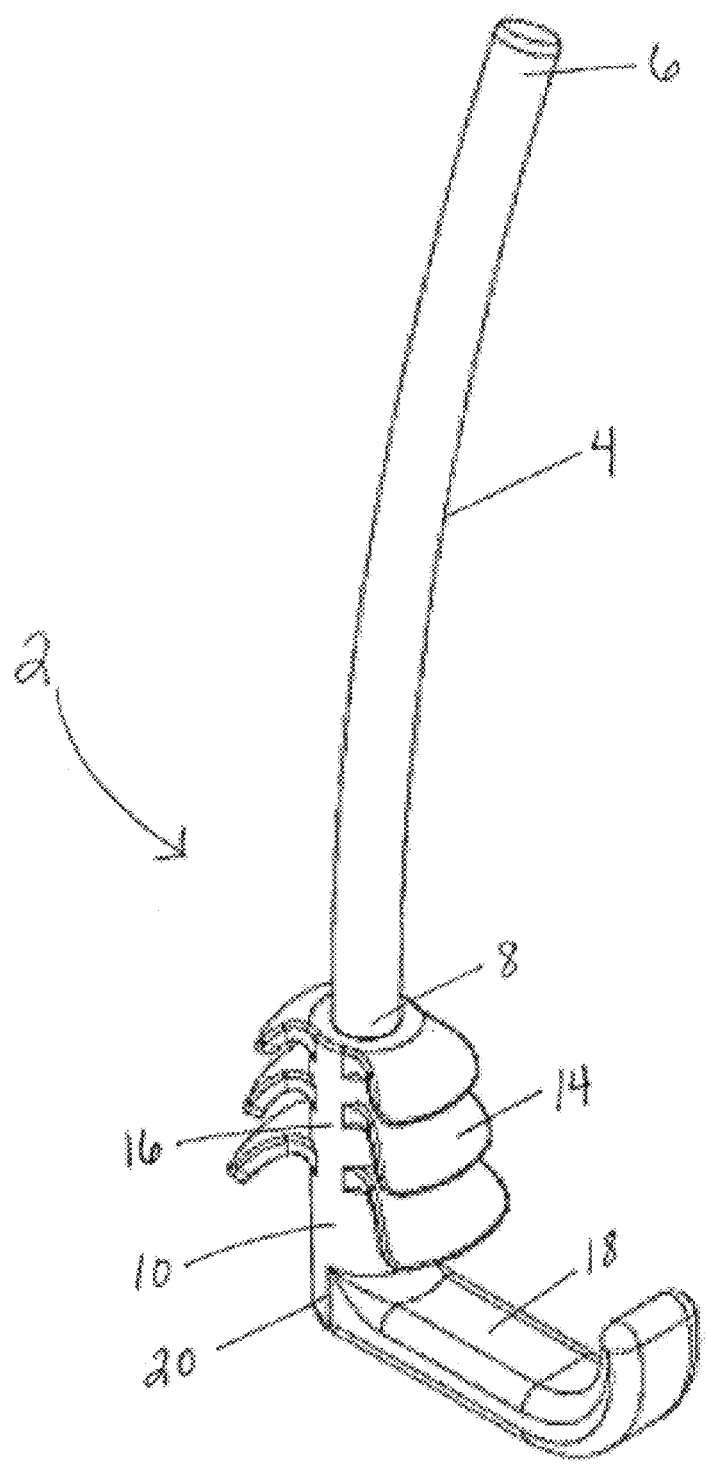
FIG. 1 is an isometric view of a nasal airway device of the present disclosure including a tube and an attachment mechanism.
Figure 2:
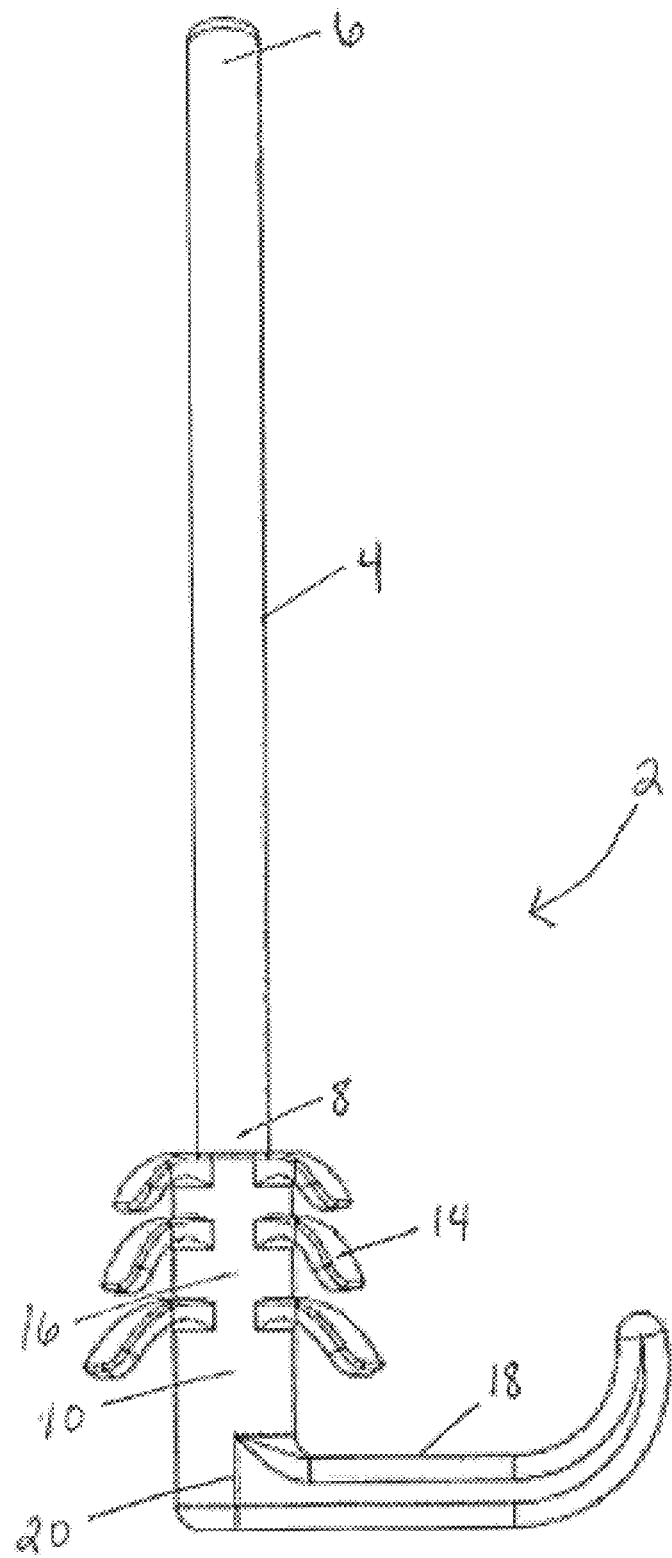
FIG. 2 is a front view of the nasal airway device of FIG. 1.
Figure 3:
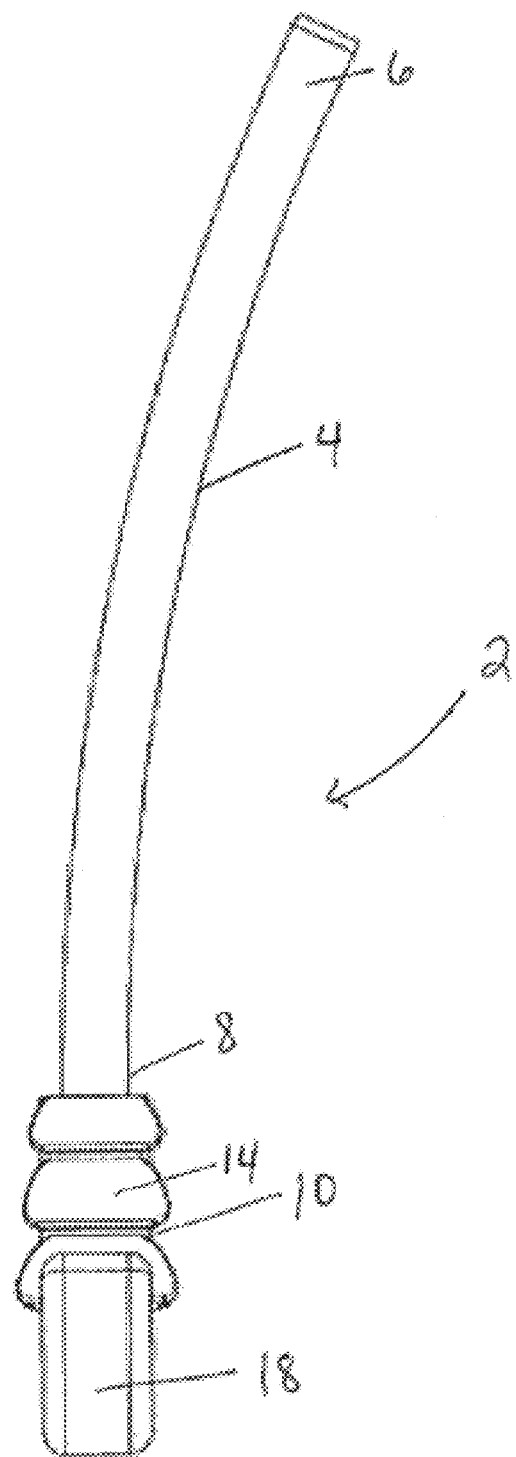
FIG. 3 is a right side view of the nasal airway device of FIGS. 1 and 2.
Figure 4:
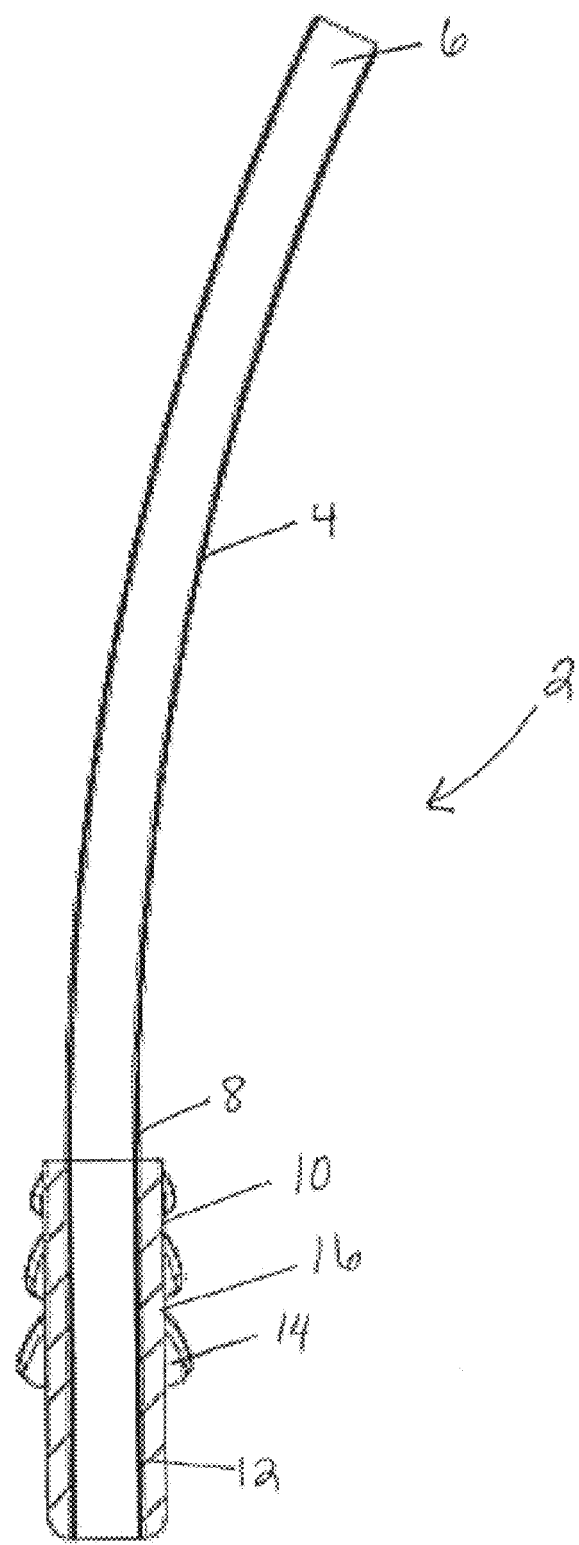
FIG. 4 is a cross-sectional left side view of the nasal airway device of FIGS. 1-3.

Embodiments within the scope of the present disclosure are directed to a nasal airway device attachment mechanism, a nasal airway device, and a nasal airway device kit including a nasal airway device and a stylet. The disclosed nasal airway device attachment mechanism, device, and kit provide a number of advantages over previously used systems. The attachment mechanism, device, and kit provide an alternative for airway patency through the nostril and mitigate the need for aggressive procedural interventions when a patient has an upper airway obstruction but maintains their own respiratory drive. The nasal airway device attachment mechanism, device, and kit are easier to use than past systems. The time to place the tube is decreased. The device is safer than existing alternatives as it does not allow the tube with the attachment in place to be pushed too far into the nasal airway. Minimal training is needed, and the amount of time spent managing the nasal airway is reduced as no additional adjustments for fixation are needed. The device can be used for more than 24 hours and can be replaced weekly or at another desired frequency. Further, the nasal airway device reduces skin damage and increases the comfort of a patient. The device is secured to the nostril and does not cause the skin damage caused by, for example, the commonly used safety pin and tape securement method.

The nasal airway device attachment mechanism, device, and kit are useful for all patients but may be particularly useful for pediatric patients with upper airway obstruction who are eligible for nasopharyngeal airway management. The attachment mechanism and device provide a tape-free securement process to avoid facial tissue damage on a pediatric patient's sensitive skin, and therefore prevents necrosis. The attachment mechanism and device reduce accidental tube extubation, enhance fit and comfort, and mitigate the need of aggressive procedural intervention, all of which are particularly valuable for pediatric patients.

One aspect of the disclosure is directed to a nasal airway device attachment mechanism configured to secure around and couple to a proximal end of a nasal tube or other hollow tube. The attachment mechanism includes a tube access channel, a plurality of fins on an exterior surface of the tube access channel, at least one of the plurality of fins being deformable, and a bridge connected at a proximal portion of the exterior surface of the tube access channel. The plurality of fins may be straight, curved, or a combination thereof.

Another aspect of the disclosure is directed to a nasal airway device, which includes a nasal tube having a hollow lumen. The tube has a distal end and a proximal end. An attachment mechanism is coupled to the proximal end of the tube. The attachment mechanism includes a tube access channel, a plurality of fins on an exterior surface of the tube access channel, at least one of the plurality of fins being deformable, and a bridge connected at a proximal portion of the exterior surface of the tube access channel. The plurality of fins may be straight, curved, or a combination thereof.

The nasal airway device kit of another aspect of the disclosure includes a nasal airway device and a stylet. Specifically, in at least some embodiments, the nasal airway device kit includes a tube having a distal end, a proximal end, an external diameter, and an internal diameter, an attachment mechanism coupled to the proximal end of the tube, the attachment mechanism including a tube access channel having an interior diameter that is greater than the external diameter of the tube or can expand to accommodate the external diameter of the tube, a plurality of fins on an exterior surface of the tube access channel, at least one of the plurality of fins being deformable, and a bridge connected at a proximal portion of the exterior surface of the tube access channel. The plurality of fins may be straight, curved, or a combination thereof. The nasal airway device kit further includes a stylet having an outer diameter less than the internal diameter of the tube. The tube may have an external diameter between 2 and 6 mm.

In some embodiments of the nasal airway device attachment mechanism, device, and kit, the fins may be only semi-occluding in order to allow nasal discharge to flow out of the nostril during device use. This is an important feature for long-term use of the device. To achieve a semi-occluding arrangement, the fins may be spaced around a circumference of the exterior surface of the tube access channel by one or more angles. Nasal discharge may be expelled through the gaps formed by the angles. Alternately or in addition, at least one of the fins may include one or more cutouts through which nasal discharge may be expelled.

The fins may connect to the exterior surface of the tube access channel in a variety of ways. At least one of the fins may connect to the exterior surface of the tube access channel at a connection end and have a free end that protrudes out from the exterior surface of the tube access channel at an angle ranging from 0 to 180 degrees. At least one of the fins may connect to the exterior surface of the tube access channel at the first end and second end. Further, at least one of the fins may connect to the exterior surface of the tube access channel so as to create an enclosed volume between the exterior surface of the tube access channel and the fin. The fins may be adjustable via at least one of air pressure, fluid pressure, and mechanical supports. For example, a fin may have a free end propped upward by a wedge. The geometrical features of the attachment mechanism or its deformability may also be used to adjust the fins. Alternately, a fin may have a first end connected to a sliding member, which surrounds or is otherwise configured to slide in or on the tube access channel or tube, and a second end connected to the exterior surface of the tube access channel. Movement of the sliding member may adjust the width of the fin from a wide position to a narrow position or to any width in-between. Additionally, a fin may have an enclosed volume that operates like a balloon and can be adjusted in size by adding or removing air. The fins may include at least one of an adhesive to improve securement, surface texture for increasing friction, thermal expanding members that grow in the presence of heat, and moisture-sensitive expanding members that grow in the presence of moisture.

In some embodiments of the nasal airway device attachment mechanism, device, and kit, the bridge may extend in a first direction away from the exterior surface of the tube access channel. For example, the bridge may be configured to extend across the nasal septum of a patient. In other embodiments, the bridge may extend both in a first direction and in a second direction away from the exterior surface of the tube access channel. That is, for example, the bridge may have a first portion extending in a first direction that is configured to extend across the nasal septum of a patient and a second portion extending in a second direction that is configured to extend to the outside of the patient's nose. The bridge may include a hook that curves or projects toward a distal end of the attachment mechanism. The curvature or distal projection may enable the bridge to secure the device in place by engaging a nostril or outside surface of the nose. In some embodiments, the hook may include secondary fins, which may take any of the forms described with respect to the fins. The secondary fins allow the bridge to engage the other nostril. In some embodiments, the tube access channel is a first tube access channel, and the bridge connects the first tube access channel to a second tube access channel. This enables two tubes to be secured within the nose of a patient, one within each nostril, or one tube may be secured alternately between nostrils. The second tube access channel may have a plurality of fins on an outer surface of the second tube access channel to secure it in place, at least one of the plurality of fins being deformable.

For purposes of placing the nasal airway device, at least one of the stylet and the tube may have a rounded tip or another preferred geometry, such as a taper, to facilitate insertion into the nose. The tube may also have a curvature to facilitate insertion into the nose. At least one of the stylet and the tube may include a thermoplastic material with low surface friction. The stylet may include a placement aid, such as a light source or audio speaker, to help with positioning.

A variety of different materials may be used to form the nasal airway device and associated components. In some embodiments, the attachment mechanism includes at least one of medical grade silicone elastomer and thermoplastic elastomer. In some embodiments, the bridge includes a ductile material that holds its shape once deformed. The tube may include medical grade PVC, silicone, or another semi-rigid thermoplastic. The tube may have hybrid or heterogeneous material properties with locally variable stiffness.

Referring to the figures in detail, FIGS. 1-4 illustrate an exemplary nasal airway device 2. The nasal airway device 2 has a tube 4 having a distal end 6 and a proximal end 8. The tube 4 may have hybrid or heterogeneous material properties with locally variable stiffness. The tube may include medical grade PVC, silicone, or another semi-rigid thermoplastic. An attachment mechanism 10 is coupled to the proximal end 8 of the tube 4. In some examples, the attachment mechanism 10 and the tube 4 are separate elements that are coupled. In other examples, the attachment mechanism 10 and the tube 4 are integrally formed. The attachment mechanism 10 includes a tube access channel 12, fins 14 on an exterior surface 16 of the tube access channel 12, and a bridge 18 attached at a proximal portion 20 of the exterior surface 16 of the tube access channel 12. When the tube 4 is placed in a patient, the fins 14 rest within the nostril of the patient and the bridge 18 extends across nasal septum of the patient. The attachment mechanism 10 may include at least one of medical grade silicone elastomer and thermoplastic elastomer. In some embodiments, the attachment mechanism 10 is removably coupled to the tube 4.

Figure 5:
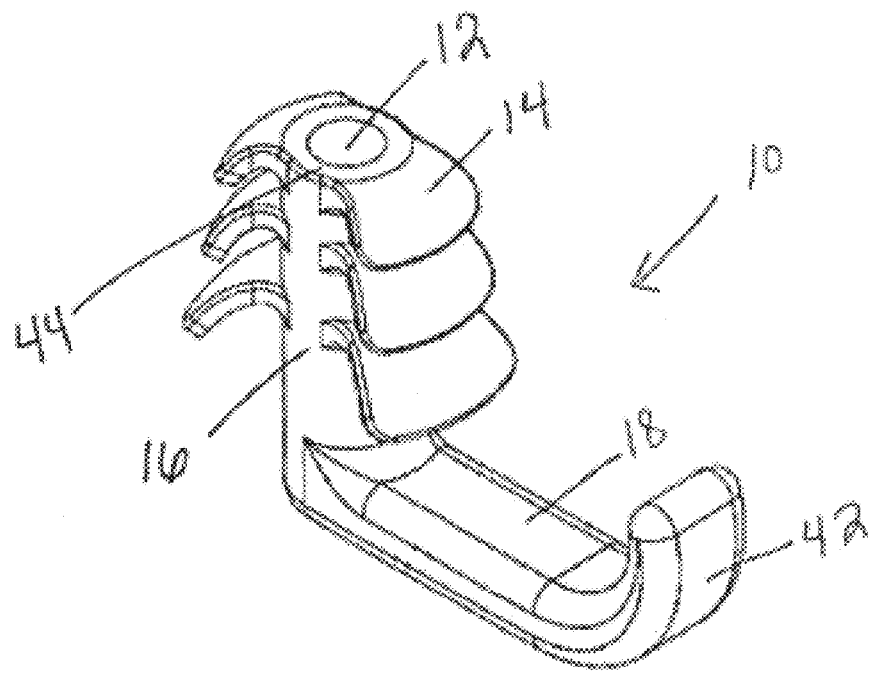
FIG. 5 is an isometric view of an attachment mechanism of the present disclosure including a tube access channel, fins, and a bridge.
Figure 6:
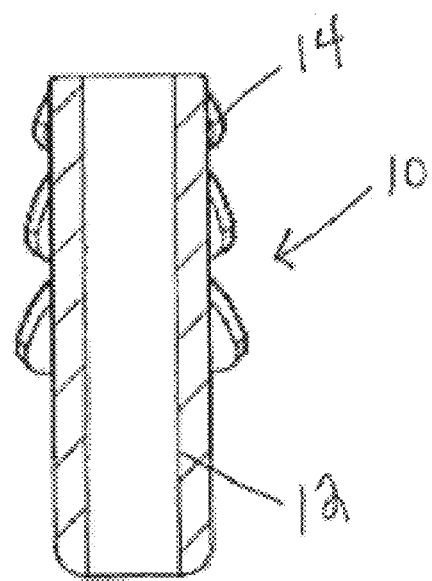
FIG. 6 is a cross-sectional left side view of the attachment mechanism of FIG. 5.
Figure 7:
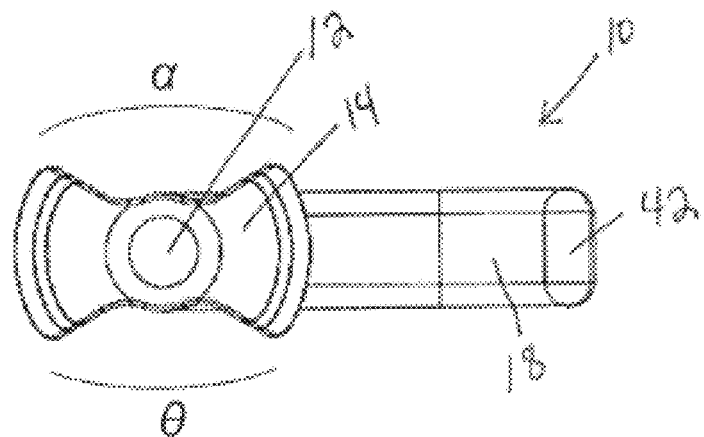
FIG. 7 is a top view of the attachment mechanism of FIG. 5 and FIG. 6 illustrating that the fins are spaced around a circumference of the tube access channel.

As shown in FIGS. 5-7, the bridge 18 of the attachment mechanism 10 may include a hook 42 that curves or projects toward a distal end 44 of the attachment mechanism 10. The bridge 18 may include a ductile material that holds its shape once deformed so that the bridge 18 can be adjusted to the particular anatomy of a patient. Additionally, the fins 14 may have a stacked configuration on the exterior surface 16 of the tube access channel 12. The fins 14 may be straight, curved, or a combination thereof. In the example shown in FIG. 5, the attachment mechanism 10 has three fins 14 stacked on one side of the exterior surface 16 and another three fins 14 stacked on the other side of the exterior surface 16.

Figure 8:
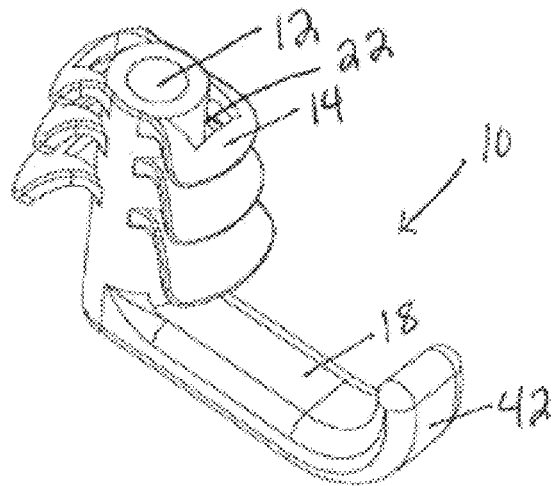
FIG. 8 is an isometric view of an attachment mechanism of the present disclosure including fins having a cutout.
Figure 9:
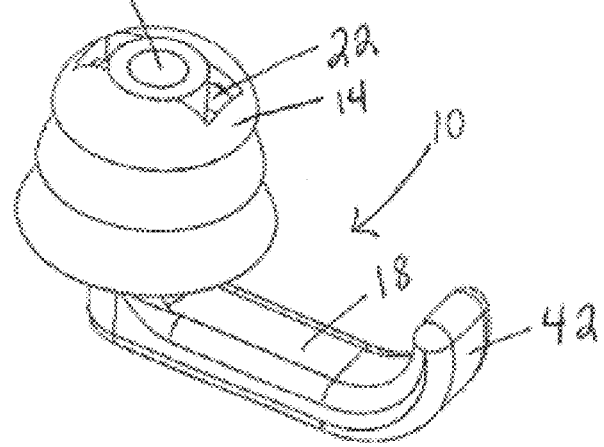
FIG. 9 is an isometric view of an attachment mechanism of the present disclosure including an alternate shape of fins having cutouts.

The fins 14 may be semi-occluding in order to allow nasal discharge to be expelled through the nostril while the nasal airway device 2 is in place. For example, in FIG. 7, the fins 14 are spaced around a circumference of the exterior surface 16 of the tube access channel 12. The fins are spaced apart by an angle $\alpha$ in on one side and an angle $\theta$ on the other side, and nasal discharge can flow through the space created by these angles. The angles $\alpha$ and $\theta$ are equal in FIG. 7. In other arrangements, the angles $\alpha$ and $\theta$ may not be equal. Moreover, in arrangements having more than two fins 14 spaced around the circumference of the exterior surface 16, the angle between any two fins 14 may be equal to or different than the angle between any other two fins 14. In some arrangements, such as those shown in FIGS. 8 and 9, the fins 14 are semi-occluding because a cutout 22 is provided in some or all of the fins 14. A single cutout 22 may be provided in each fin 14 as shown in FIG. 8, or multiple cutouts may be provided in each fin 14 as shown in FIG. 9. Also, as shown in FIG. 9, each fin 14 may be connected to the exterior surface 16 of the tube access channel 12 around the entire circumference of the exterior surface 16.

The fins 14 may be connected to the exterior surface 16 of the tube access channel 12 in a variety of manners, as shown in FIGS. 10A, 10B-15. As shown in FIGS. 10A, 10B-12, the fins 14 may be connected to the exterior surface 16 of the tube access channel 12 at a connection end 24 and may have a free end 26 that protrudes out from the exterior surface 16 of the tube access channel 12 at an angle φ ranging from 0 to 180 degrees. Preferably, the fins 14 protrude out from the exterior surface 16 of the tube access channel 12 at an angle φ ranging from 0 to 90 degrees in order to allow for insertion into the nostril and still prevent unintentional removal from the nostril. In an example, the nasal airway device 2 includes at least one fin on the exterior surface 16. However, there is no limitation on the number of the fins 14 that can be included.

Figure 10A:
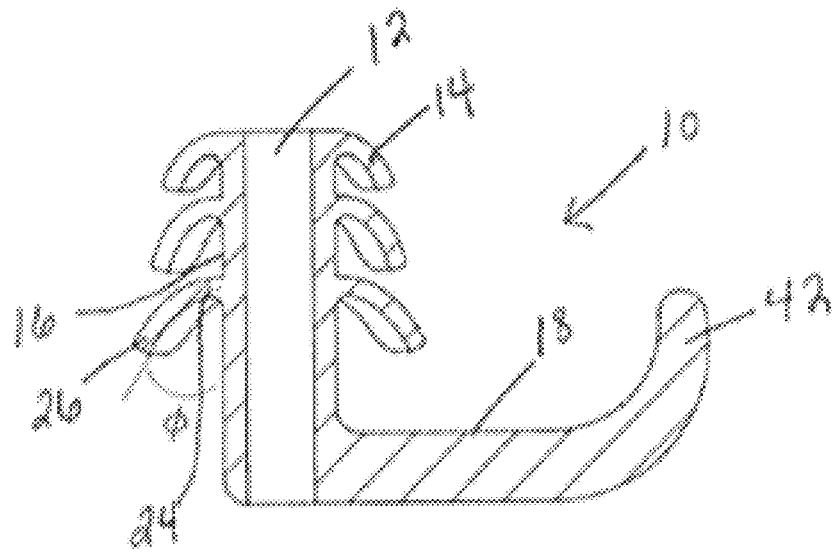
FIG. 10A is a cross-sectional front view of an attachment mechanism of the present disclosure where the fins have a connection end and a free end that protrudes out from the tube access channel.
Figure 10B:
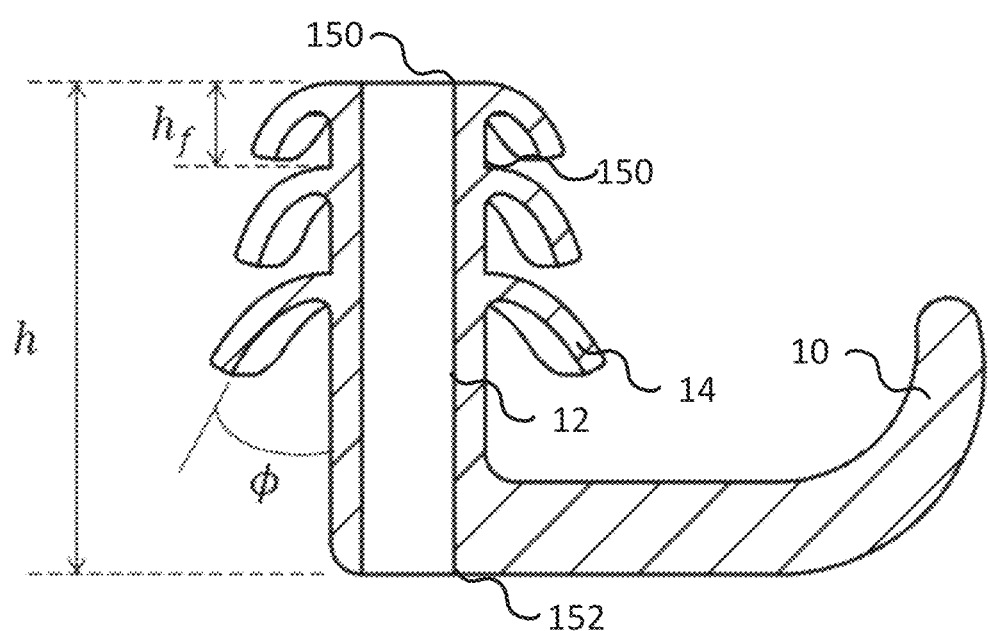
FIG. 10B is a cross-sectional front view of another attachment mechanism of the present disclosure where the fins have a connection end and a free end that protrudes out from the tube access channel.
Figure 11:
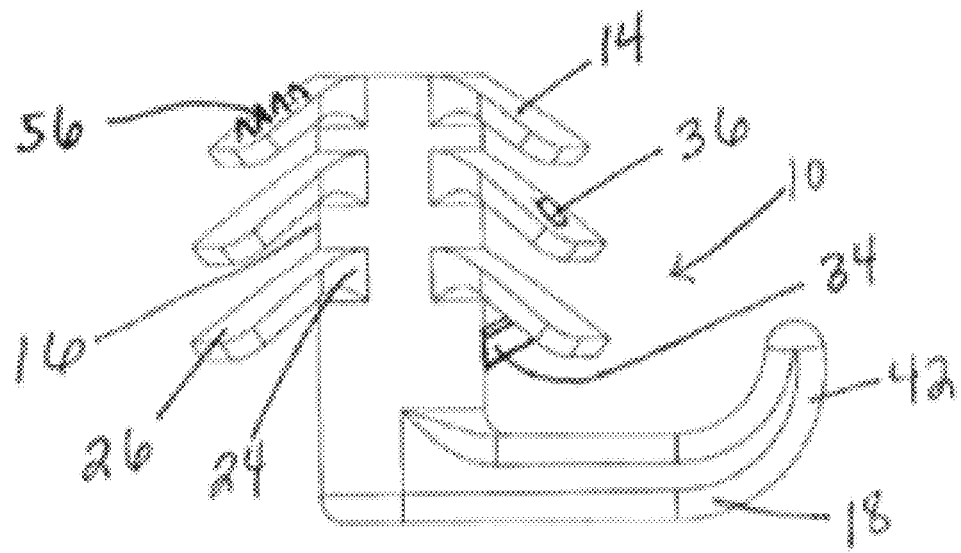
FIG. 11 is a front view of an attachment mechanism of the present disclosure where one of the fins is supported by a mechanical support and another of the fins includes an adhesive.

As shown in FIG. 10B, a total height of the attachment mechanism 10 is defined as a distance between a proximal opening 150 of the channel 12 and a distal opening 152 of the channel 12. In the example shown, each fin 14 has a height $h_f$ defined as a distance between the proximal opening 150 of the channel 12 and a base 154 of the fin 14 connected to the exterior surface 16. In some examples, the fins 14 have the same or similar heights $h_f$ with each other. In other examples, the fins 14 have different heights $h_f$ from each other. The $h_f$ can range from 0 to h. In an example, a range of $h_f$ is around 0 to 0.5 h.

Figure 13:
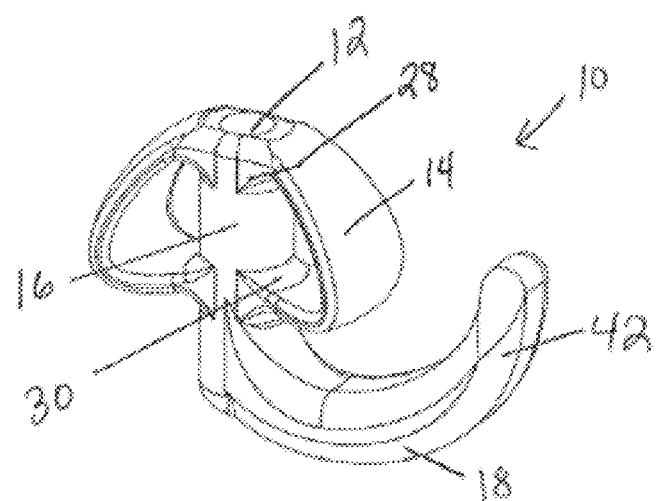
FIG. 13 is an isometric view of an attachment mechanism of the present disclosure having two fins, each of which connects to the tube access channel at a first end and a second end.
Figure 14:
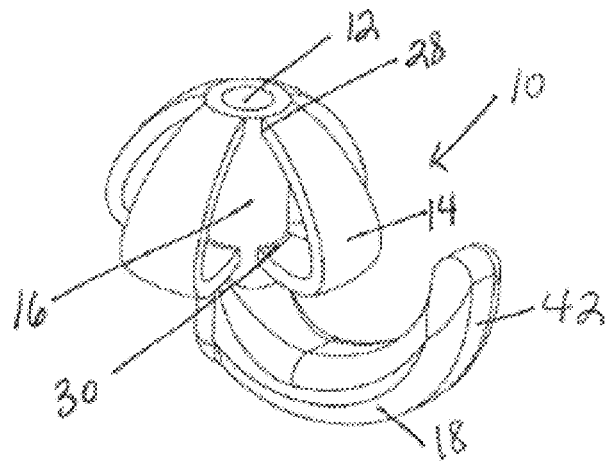
FIG. 14 is an isometric view of an attachment mechanism of the present disclosure having four fins, each of which connects to the tube access channel and a first end and a second end.
Figure 15:
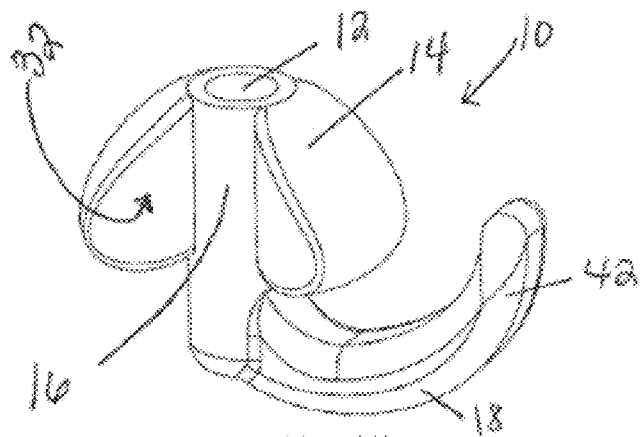
FIG. 15 is an isometric view of an attachment mechanism of the present disclosure having fins that connect to the tube access channel so as to create an enclosed volume between the tube access channel and the fin.
Figure 16A:
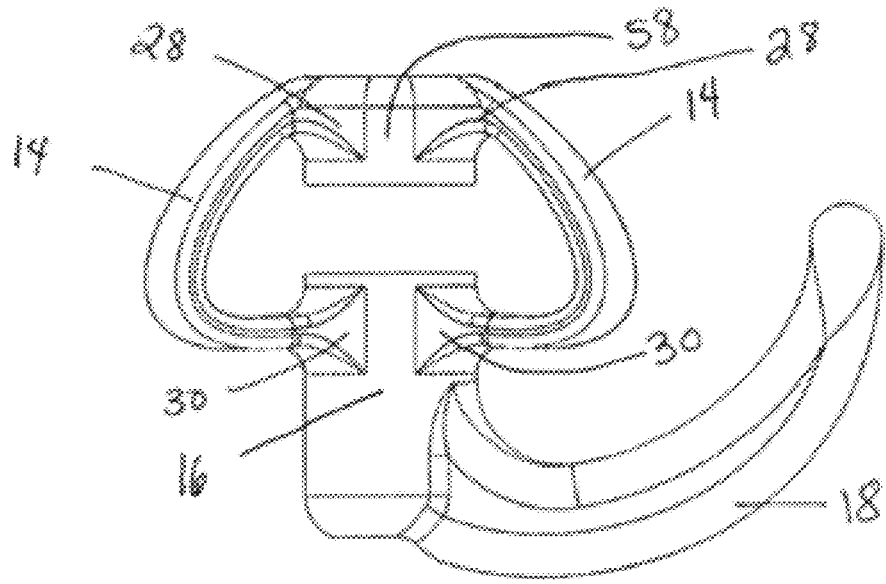
FIG. 16A is a front view of an attachment mechanism of the present disclosure having adjustable fins, each fin connected to a sliding member at a first end and to the tube access channel at a second end, the attachment mechanism depicted in a wide position.
Figure 16B:
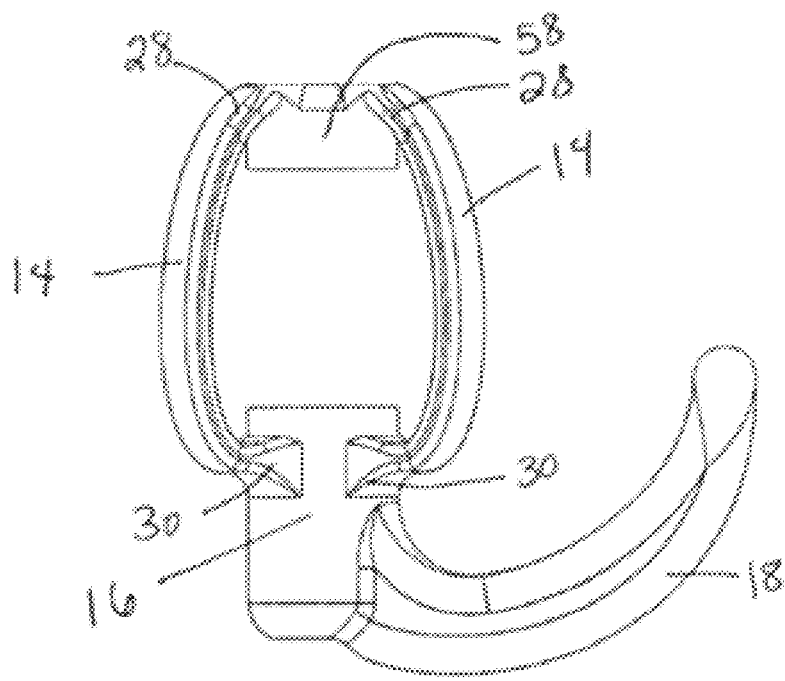
FIG. 16B is a front view of the attachment mechanism of FIG. 16A, the attachment mechanism depicted in a narrow position.
Figure 17:
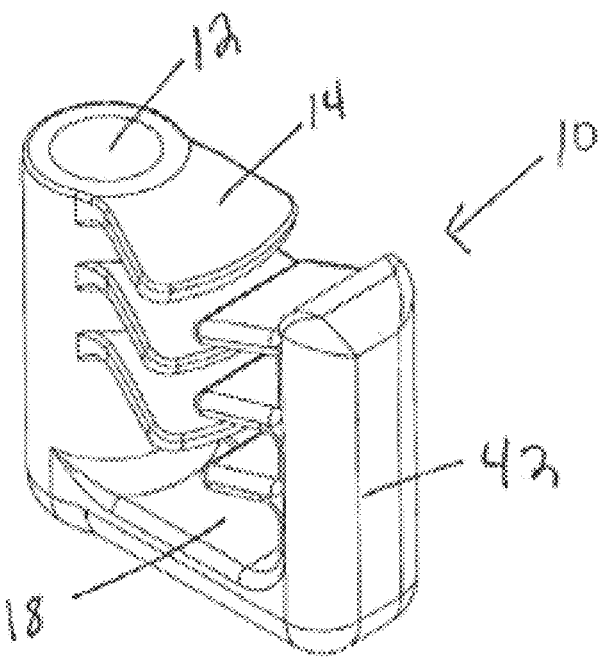
FIG. 17 is an isometric view of an attachment mechanism of the present disclosure having three fins and a bridge including a hook with three secondary fins.
Figure 18:
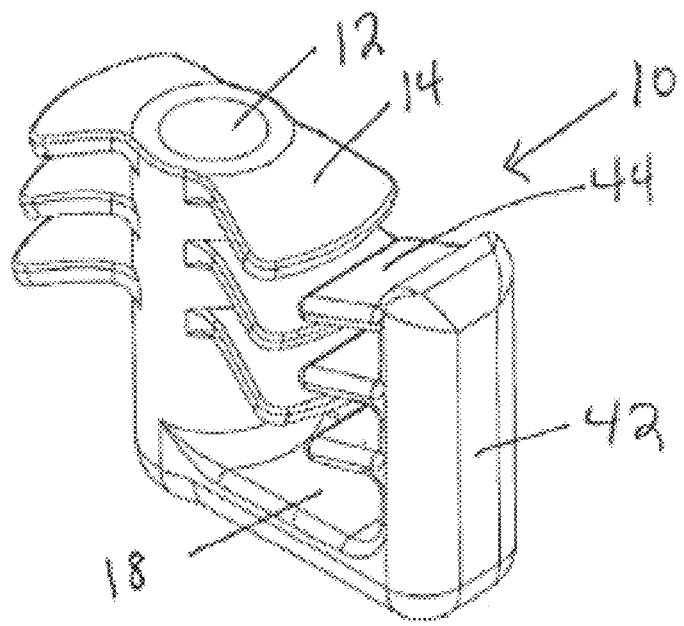
FIG. 18 is an isometric view of an attachment mechanism of the present disclosure having six fins and a bridge including a hook with three secondary fins.
Figure 19:
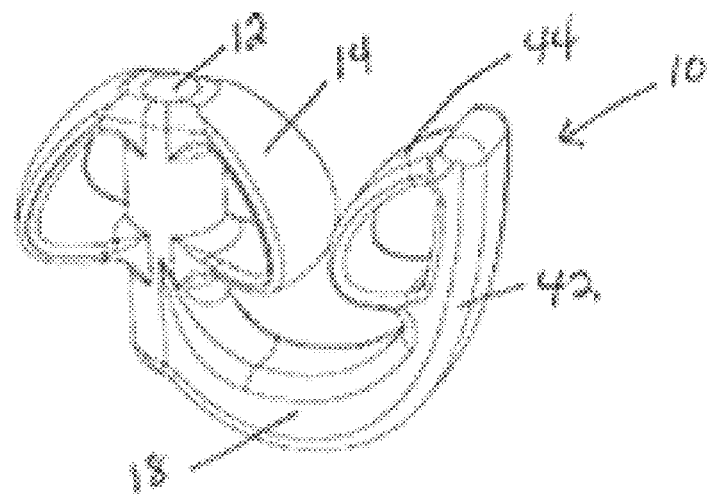
FIG. 19 is an isometric view of an attachment mechanism of the present disclosure having two fins and a bridge including a hook with one secondary fin.

As shown in FIGS. 13 and 14, the fins 14 may connect to the exterior surface 16 of the tube access channel 12 at both a first end 28 and a second end 30. As shown in FIG. 15, the fins 14 may connect to the exterior surface 16 of the tube access channel 12 so as to create an enclosed volume 32 between the exterior surface of the tube access channel 12 and the fin 14. The fins 14 may be adjustable. For example, a mechanical support such as that shown in FIG. 11 may be used to adjust the angle that a fin 14 is attached to the exterior surface 16 of the tube access channel 12. Air pressure or fluid pressure may be used to adjust the enclosed volume 32 of a fin 14 such that the fin 14 is essentially a balloon that is expanded to a final shape by an air or fluid pump system. As shown in FIGS. 16A and 16B, a fin 14 may have a first end 28 connected to a sliding member 58, which surrounds or is otherwise configured to slide in or on the tube access channel 12 or the tube 4. The fin 14 may have a second end 30 connected to the exterior surface 16 of the tube access channel 12. Movement of the sliding member 58 on the tube access channel 12 or tube 4 may adjust the width of the fins 14 from a wide position (shown in FIG. 16A) to a narrow position (shown in FIG. 16B) or to any width in-between.

Figure 12:
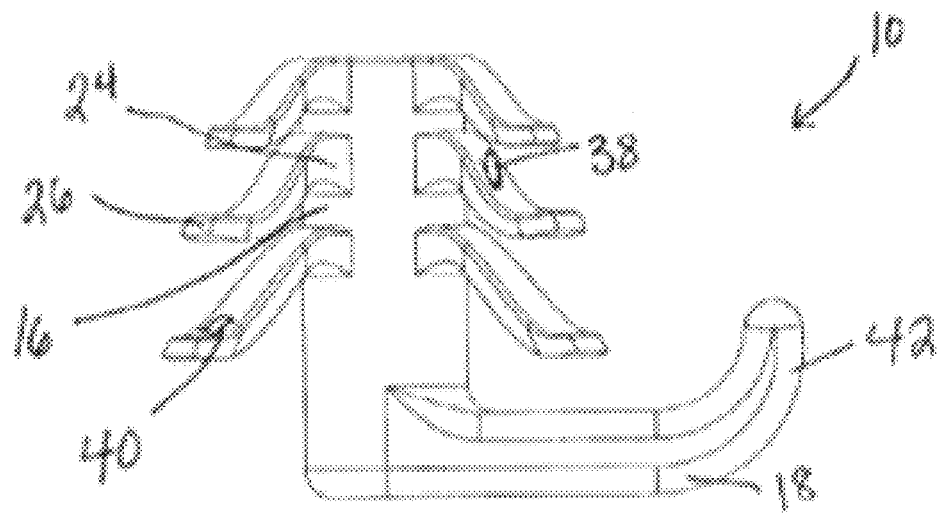
FIG. 12 is a front view of an attachment mechanism of the present disclosure where one of the fins includes a thermal expanding member and another of the fins includes a moisture-sensitive expanding member.

The fins 14 may have expanding members, such as thermal-expanding member 38 and moisture-sensitive expanding member 40 shown in FIG. 12, that react to environmental conditions of the nose such as heat or moisture in order to expand and secure the attachment mechanism 10 in place. An adhesive, such as adhesive 36 in FIG. 11, or surface texture, such as surface texture 56 in FIG. 11, may be provided on one or more of the fins 14 in order to improve securement of the attachment mechanism 10 within the nostril.

Figure 20:
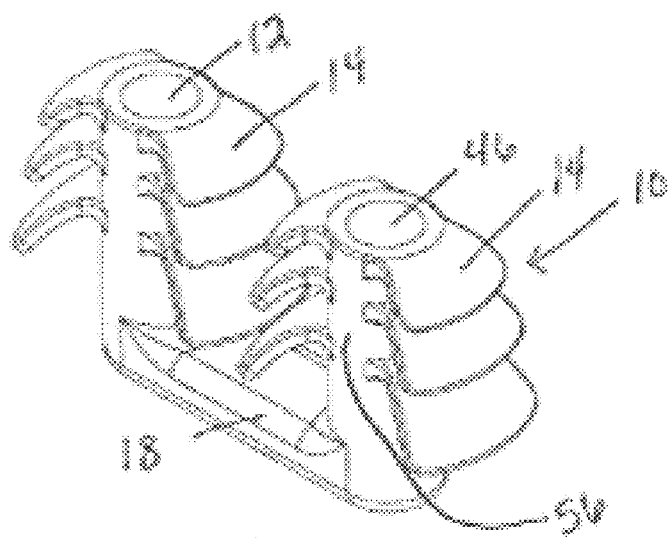
FIG. 20 is an isometric view of an attachment mechanism of the present disclosure having a first tube access channel and a second tube access channel connected by a bridge.
Figure 21:
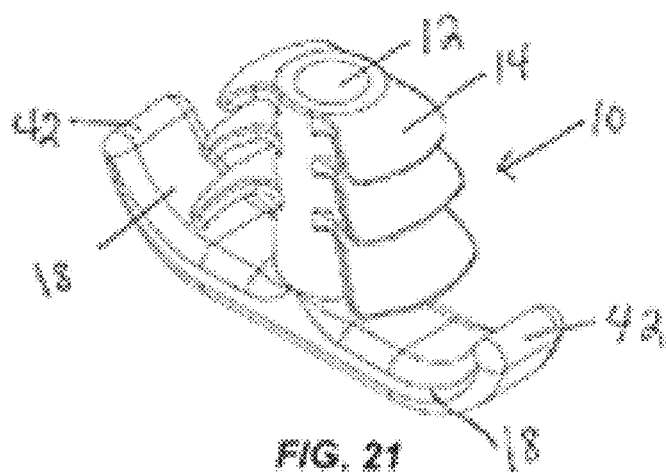
FIG. 21 is an isometric view of an attachment mechanism having a bridge extending in both a first direction and in a second direction away from the tube access channel, where the first direction and second direction are 180 degrees from one another.
Figure 22:
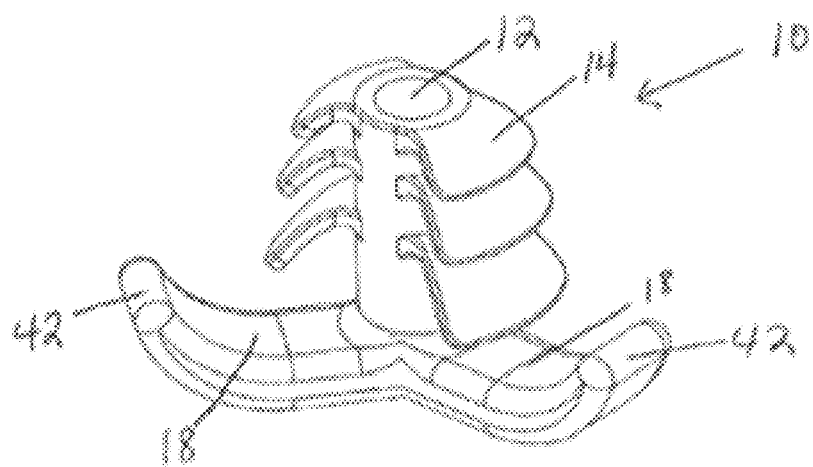
FIG. 22 is an isometric view of an attachment mechanism having a bridge extending in both a first direction and in a second direction away from the tube access channel, where the first direction and the second direction are less than 180 degrees from one another.
Figure 23A:
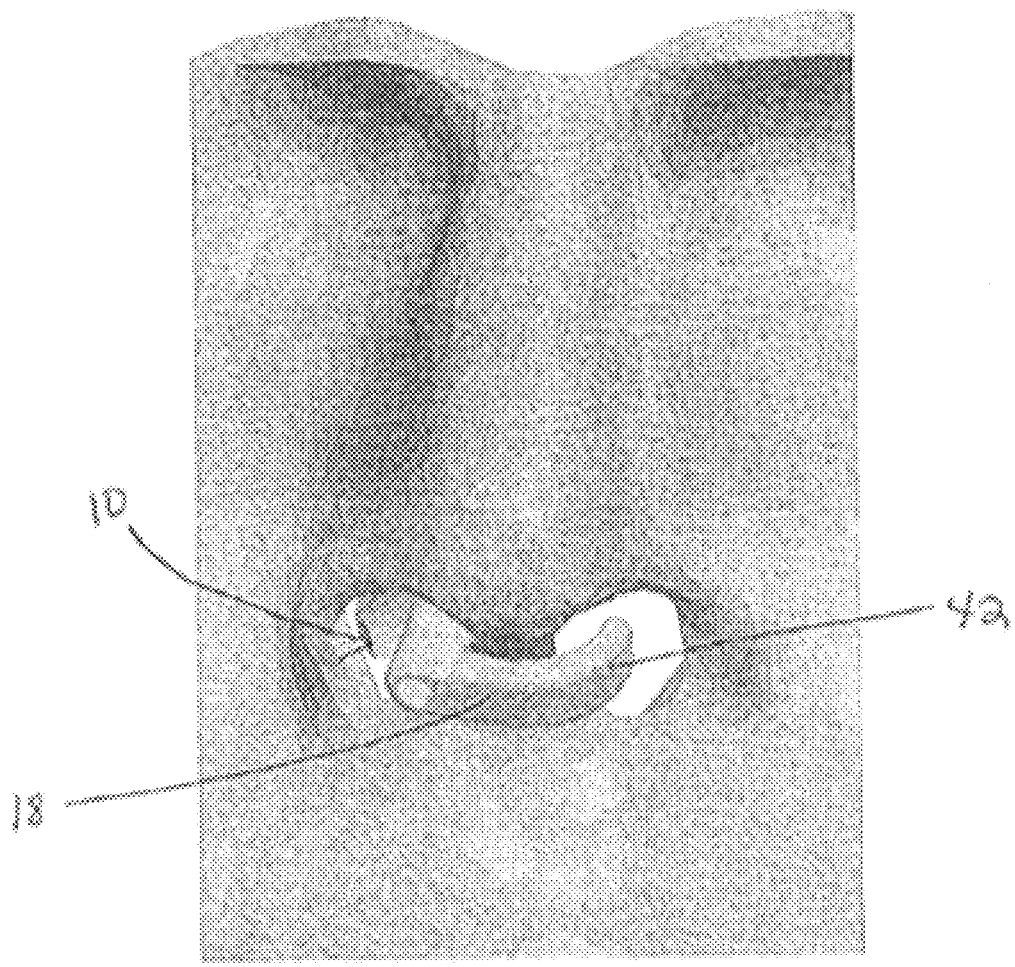
FIG. 23A illustrates an attachment mechanism with a bridge extending only in a first direction placed on a patient with the bridge extending across the nasal septum.
Figure 23B:
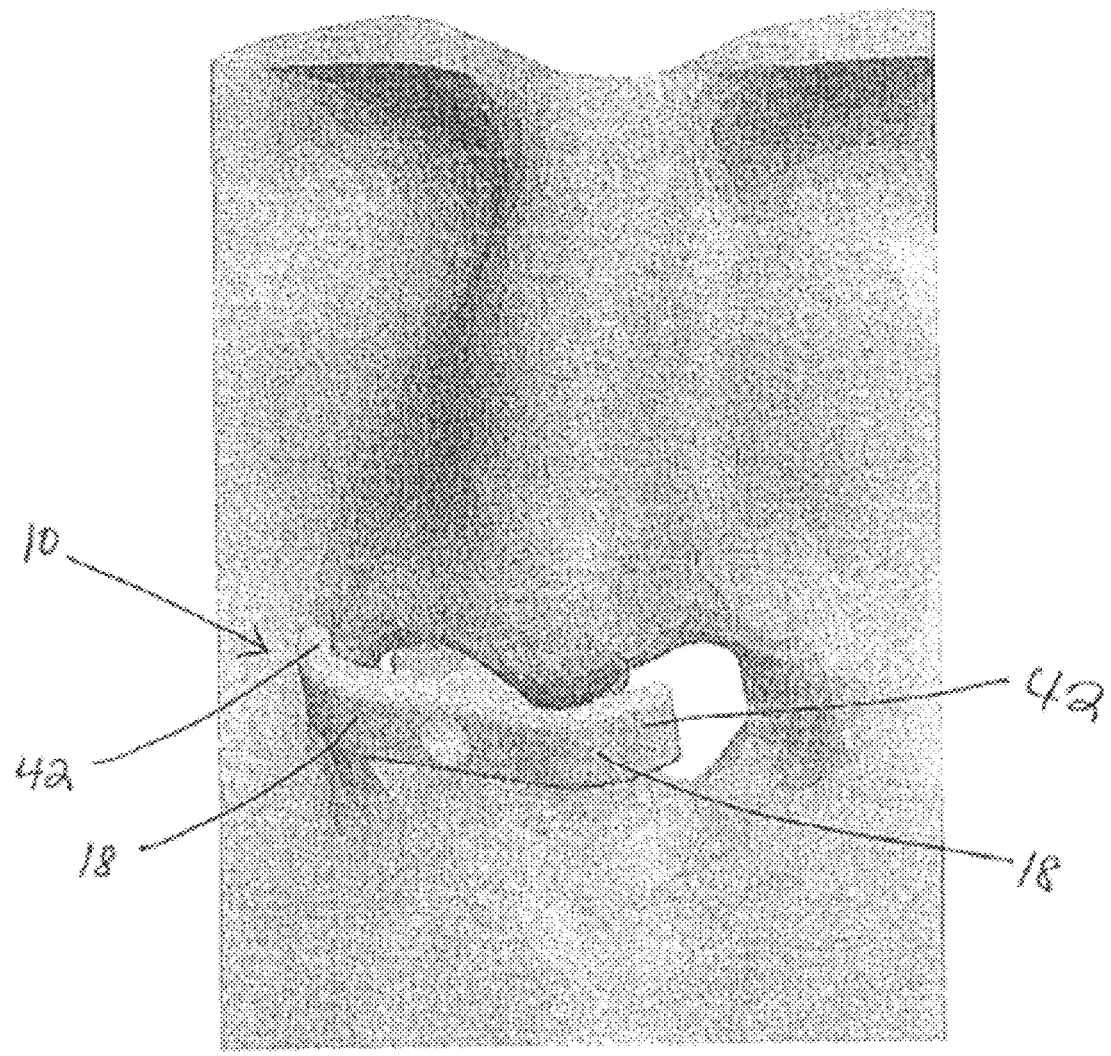
FIG. 23B illustrates an attachment mechanism with a bridge extending in a first direction and in a second direction placed on a patient with the bridge extending across the nasal septum in the first direction and to the outside of the nose in the second direction.

The bridge 18 may have a variety of configurations. The bridge 18 may have a hook 42, which may curve gently or sharply or have a projection at a sharp or gentle angle. Examples of various configurations of hook 42 are depicted in FIGS. 5, 7, 8, 9 and 10A, 10B-23A, 23B, 24A, 24B, 24C. The bridge 18 may extend only in a first direction away from the exterior surface 16 of the tube access channel 12 as shown in FIGS. 5, 7-19, and 23A. Alternately, the bridge 18 may extend in both a first direction and in a second direction away from the exterior surface 16 of the tube access channel 12, as shown in FIGS. 21, 22, and 23B. The bridge may extend in additional directions, and the angle between the directions may be equal or may vary. The hook 42 may include secondary fins 44. The secondary fins 44 may have any of the configurations and arrangements described with respect to the fins 14. FIG. 20 depicts an attachment device 10 where the tube access channel 12 is a first tube access channel, and the bridge 18 connects the first tube access channel 12 to a second tube access channel 46. The second tube access channel 46 may have fins 14 on an outer surface 56. FIGS. 23A and 23B illustrate how the bridge 18 helps to secure the attachment mechanism 10 in a patient's nose. As shown in FIG. 23A, a bridge 18 that extends only in a first direction may extend across patient's nasal septum, and the hook 42 of the bridge 18 may be placed in a nostril. As shown in FIG. 23B, a bridge 18 that extends in a first direction and a second direction may extend across a patient's nasal septum in the first direction and to the outside of the patient's nose in the second direction. One hook 42 may be placed in a nostril, and another hook 42 may wrap around the outside of the patient's nose. Other placements of a bridge 18 with respect to a patient's anatomy are within the scope of this disclosure.

Figure 24A:
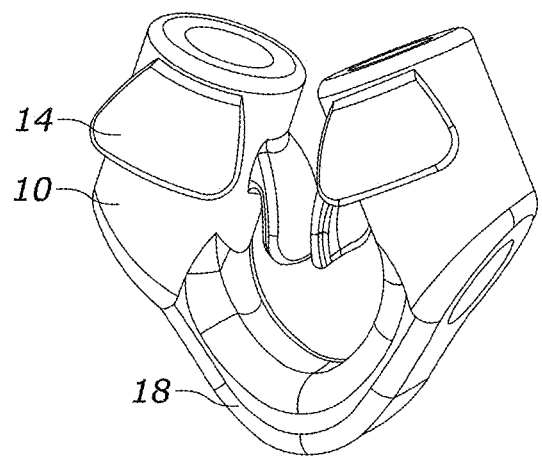
FIG. 24A is an isometric view of an attachment mechanism of the present disclosure having a first tube access channel and a second tube access channel connected by a bridge.
Figure 24B:
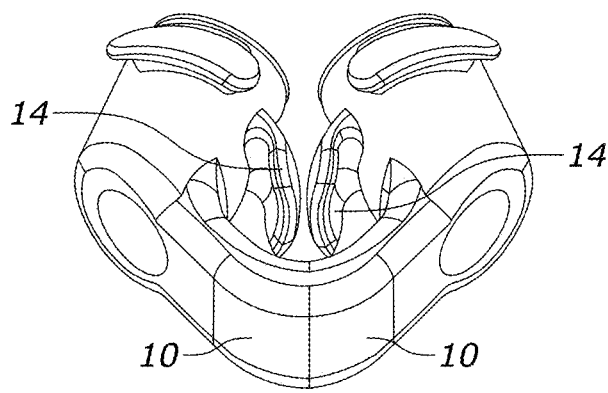
FIG. 24B is a bottom-up isometric view of the attachment mechanism of FIG. 24A.
Figure 24C:
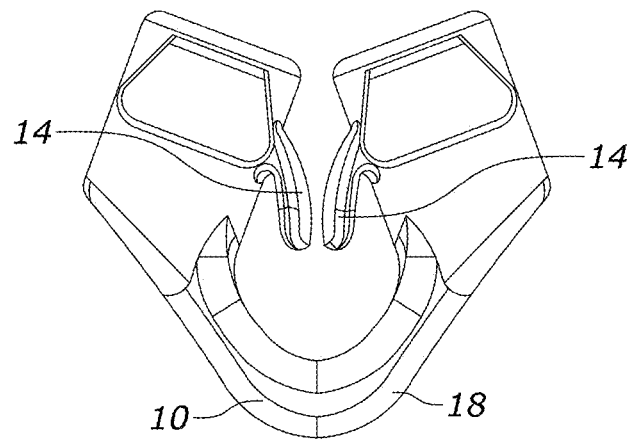
FIG. 24C is side view of the attachment mechanism of FIG. 24A.

FIGS. 24A, 24B and 24C illustrates another attachment mechanism 10 including fins 14 on a front of the attachment mechanism that may be used to hold the attachment mechanism 10 in the alar rim of the patient while the two fins 14 facing each other may create a compressive holding force on the nasal septum and columella.

Placement of the nasal airway device 2 may be facilitated by a stylet 48, which together with the attachment mechanism 10 and tube 4 of the nasal airway device 2 may form a nasal airway device kit as shown in FIGS. 25-28. The stylet 48 is first inserted into a patient's nasal passageway. If desired, the stylet 48 can act as a measurement guide and can be pulled out to determine the best length of the tube 4 for the patient's anatomy. The tube 4 can be trimmed to an optimal length for the patient's anatomy, and the attachment mechanism 14 can be fixed to the proximal end of the tube 4 by a press fit or other suitable means. The stylet 48 is inserted into the patient's nasal passageway to function as a guide. The tube 4 is then inserted over the stylet 48, and the attachment mechanism 10 is properly positioned at the patient's nostril opening. The stylet 48 can then be removed.

Figure 25:
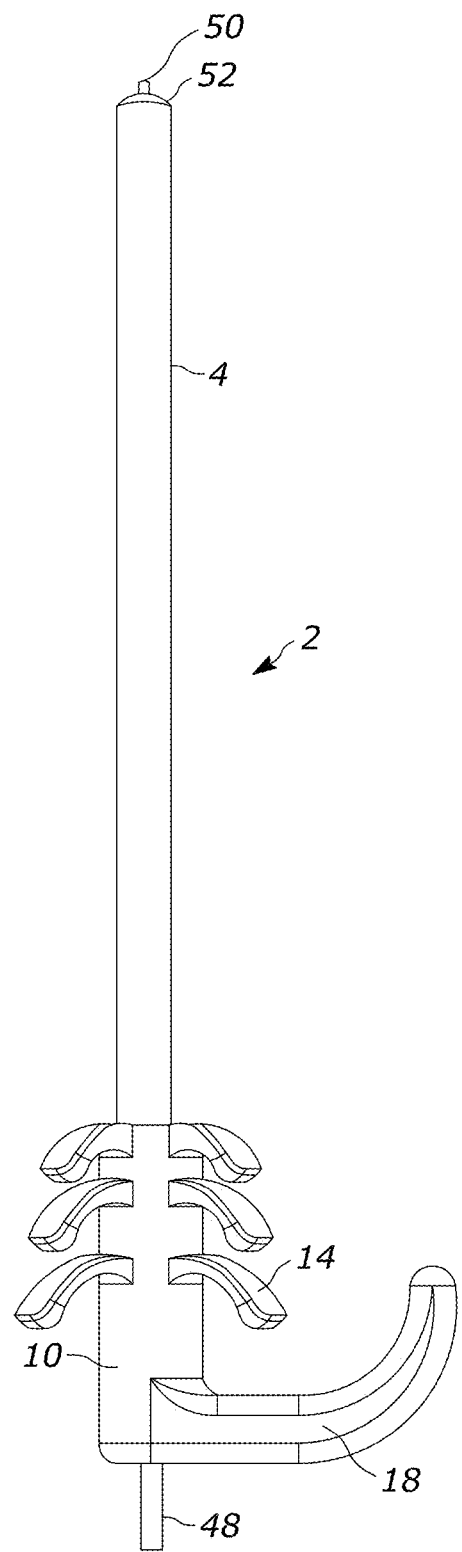
FIG. 25 is a front view of a nasal airway device kit of the present disclosure including a nasal airway device and a stylet.
Figures 26, 27, 28:
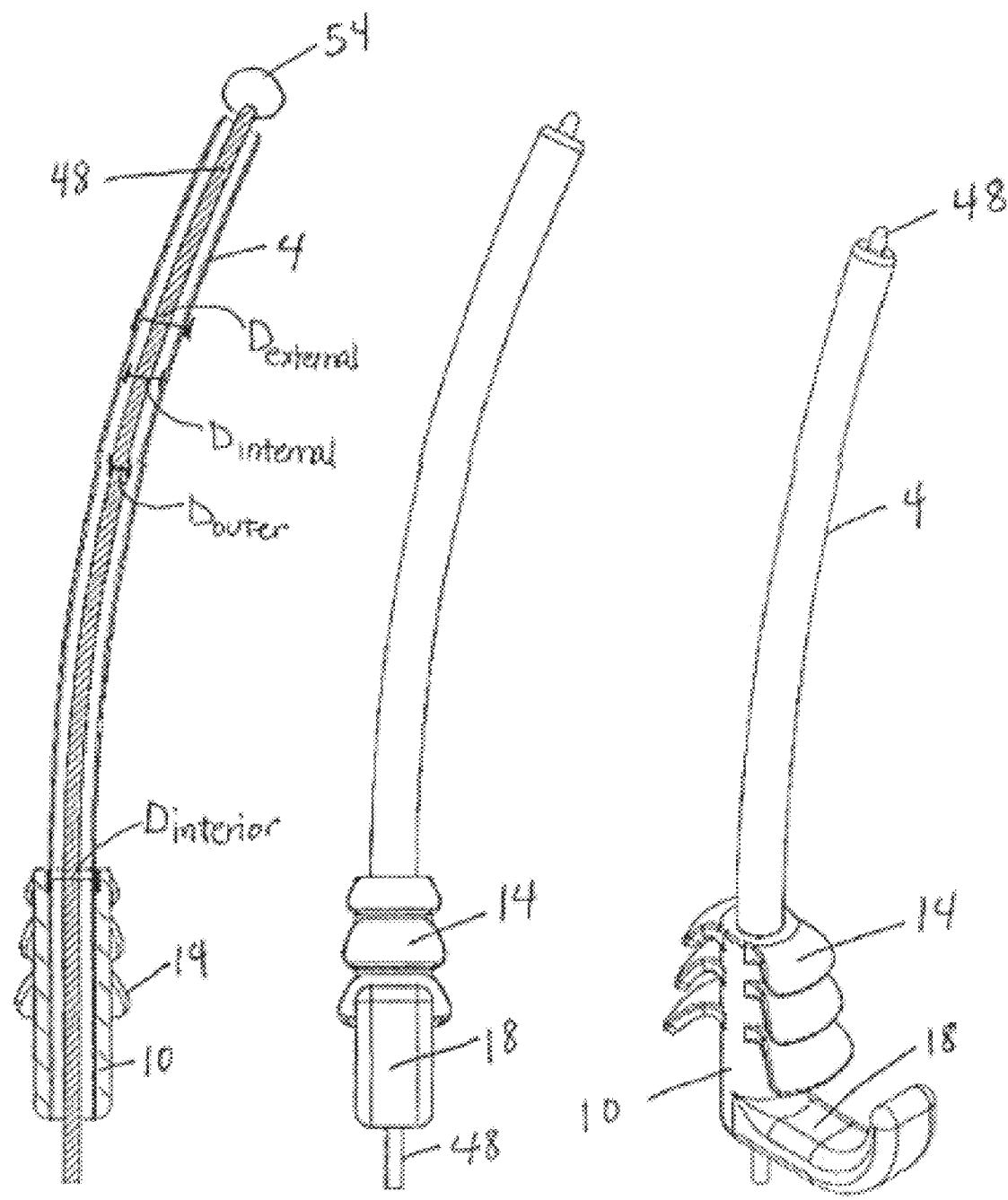
FIG. 26 is a cross-sectional left side view of the nasal airway device kit of FIG. 25.
FIG. 27 is a front view of the nasal airway device kit of FIG. 25 and FIG. 26.
FIG. 28 is an isometric view of the nasal airway device kit of FIGS. 25-27.

As shown in FIG. 25, the stylet 48 may have a rounded tip 50 and the tube 4 may have a rounded tip 52. The rounded tips 52 may facilitate insertion of the stylet 48 and the tube 4. Alternately, the stylet 48 and the tube 4 may have tips with another geometry to facilitate insertion into the nose, such as tapered tips. The stylet may include a thermoplastic material with low surface friction in order to allow smooth insertion into the patient and removal through the tube 4. The stylet 48 may have a placement aid 54, such as a light source or an audio speaker, to improve guidance and correct placement. As shown in FIG. 26, the tube 4 has an external diameter $D_{external}$, which will typically range between 2 and 6 mm but may be larger or smaller, and an internal diameter $D_{internal}$. The tube access channel 12 of the attachment mechanism 10 has a diameter $D_{interior}$ that is greater than the external diameter $D_{external}$ of the tube 4 so as to allow the tube 4 to be secured within the tube access channel 12. Alternately, the tube access channel 12 of the attachment mechanism 10 may have a diameter $D_{interior}$ that is smaller than the external diameter $D_{external}$ of the tube 4 but expands to accommodate the external diameter $D_{external}$ of the tube 4, ensuring a tight fit between the tube access channel 12 and the tube 4. The stylet 48 has an outer diameter $D_{outer}$ that is less than the internal diameter $D_{internal}$ of the tube 4 in order to allow the tube 4 to slide over the stylet 48 when the tube 4 is being placed in a patient and then to subsequently allow the stylet 48 to be removed from the tube 4.

FIG. 29 illustrates a nasal airway device 2900 in accordance with the teachings of the present disclosure. The nasal airway device 2900 is shown extending through a nostril 2902 and into a nasal cavity 2904 of a patient 2906. The nasal airway device 2900 includes a tube 2908 having a distal end 2910, a proximal end 2912 and an apex 2913. An attachment mechanism 2914 is coupled to the proximal end 2912 of the tube 2908 and is adapted to be inserted into the nostril 2902 of the patient 2906. While the attachment mechanism 2914 is schematically drawn in FIG. 29, the attachment mechanism 2914 may take any form including any of the attachment mechanisms disclosed herein.

The tube 2908 may have a radius of curvature of between about 1.5" and about 2" and may have a relatively high shore durometer. Having a higher shore durometer may avoid the tube 2908 collapsing within the nasal cavity 2904 of the patient 2906 and/or when the tube 2908 is being positioned within the nasal cavity 2904. The shore durometer may be between about 50 shore A hardness and about 90 shore A hardness. The tube 2908 has an inner diameter and an outer diameter. The inner diameter may be between about 1.5 millimeters (mm) and about 6 mm and the outer diameter may be between about 3 mm and about 7 mm. However, the tube 2908 may have different inner and outer diameters depending on the application.

The tube 2908 may be made of a single material or a dual-multi durometer material. When more than two materials are included, the distal end (the tip) of the tube 2908 may be overmolded. In such examples, the distal end 2910 (the tip) may have a lower shore durometer than the remainder of the tube 2908. The distal end 2910 may have a shore durometer of between about 2 shore A hardness and about 50 shore A hardness of between about 20 shore A hardness and about 50 shore A hardness. Thus, the tube 2908 may have a portion that is harder and may include a portion that is softer at the distal end 2910. The harder portion may allow the tube 2908 to be easier to insert and the softer portion may allow the tube 2908 to be atraumatic. Moreover, harder tubes may help prevent the tube 2908 from collapsing under the pressure of the soft tissues in the nasal cavity after many hours in the patient. Forming the portion of the tube 2908 of the harder material may reduce the likelihood that the tube 2908 collapses in the nostril 2902 and/or the nasal cavity 2904.

Figure 29A:
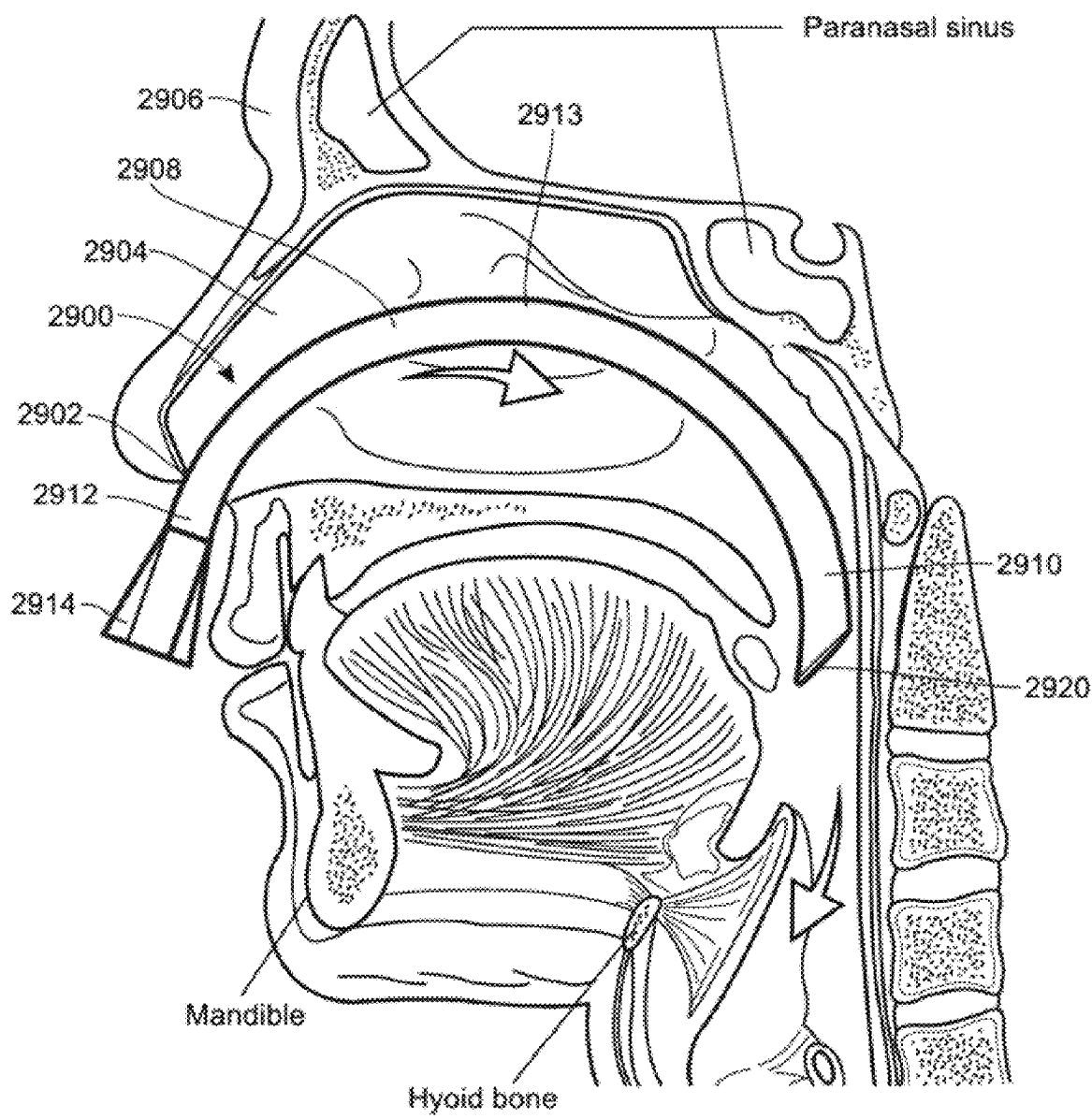
FIG. 29A illustrates a nasal airway device including a tube and an attachment mechanism in accordance with the teachings of the present disclosure.
Figure 29B:
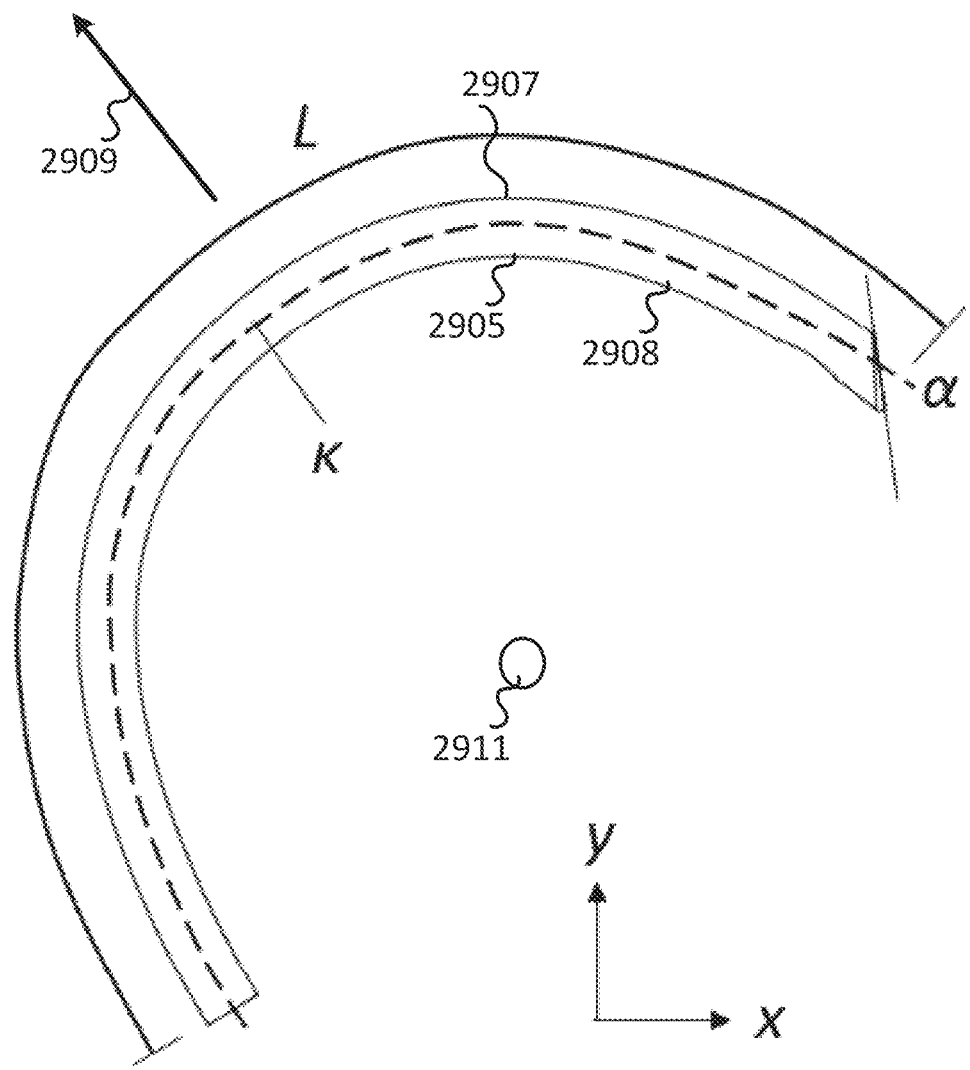
FIG. 29B illustrates a side view of the tube of FIG. 29A.
Figure 29C:
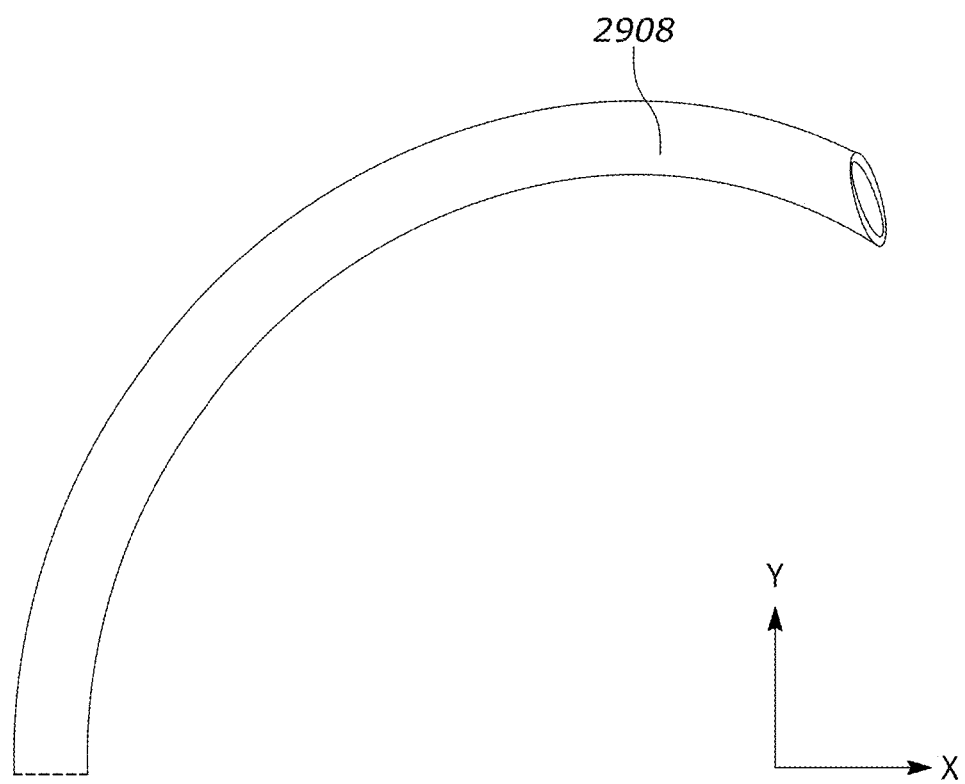
FIG. 29C illustrates an isometric view of the tube of FIG. 29A.
Figure 29D:
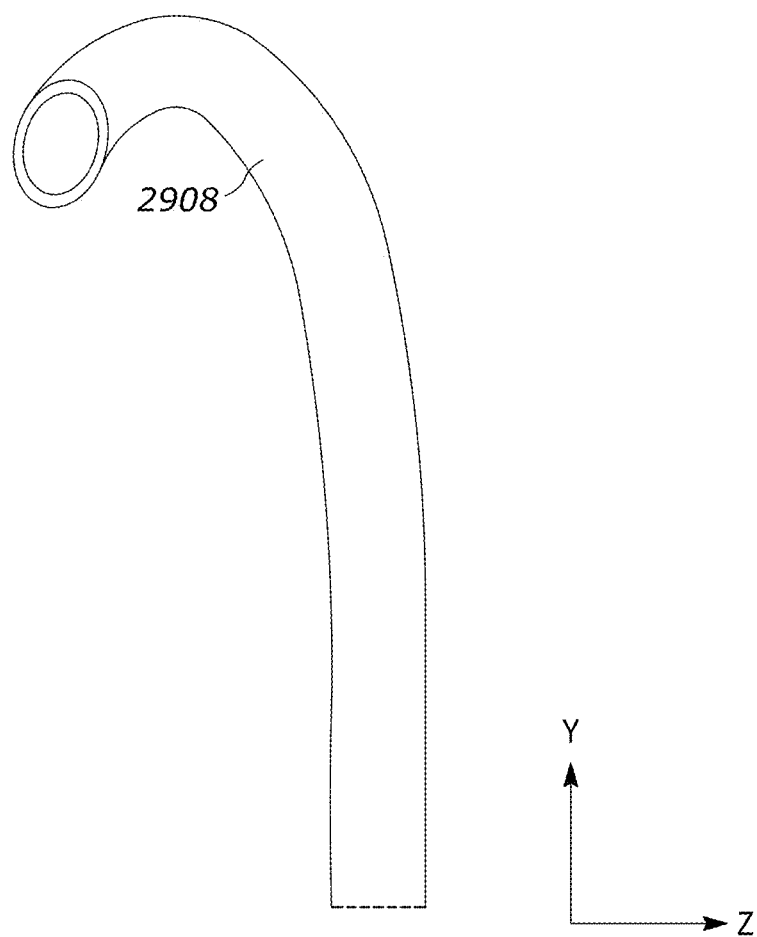
FIG. 29D illustrates another isometric view of the tube of FIG. 29A.
Figure 29E:
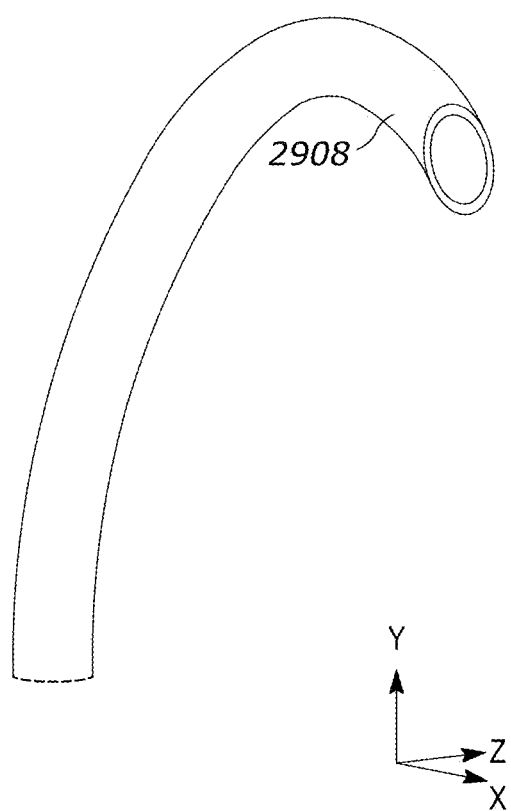
FIG. 29E illustrates another isometric view of the tube of FIG. 29A.

Referring to FIGS. 29B, 29C, 29D and 29E, the tube 2908 is illustrated having a tube centerline a with at least one curvature forming a primary curvature k (overall curvature) that forms an overall curvature with a radius of curvature relative to the tube centerline a. The primary curvature may be between about 0.030-about 0.017 mm$^{-1}$ or between about 0.010-about 0.04 mm$^{-1}$. In the example shown, the primary curvature K (the overall curvature) formed by the centerline a and is mainly on the x-y plane. However, the tube centerline a is not limited to a curve on the x-y plane. For example, the tube centerline a can be a 3D curve with the components on all axes (x, y, and z). FIG. 29C illustrates the tube 2908 in the X-Y plane, FIG. 29D illustrates the tube 2908 in the Y-Z plane and FIG. 29E illustrates the tube 2908 relative to the X-Y plane and the Y-Z plane.

Figure 29F:
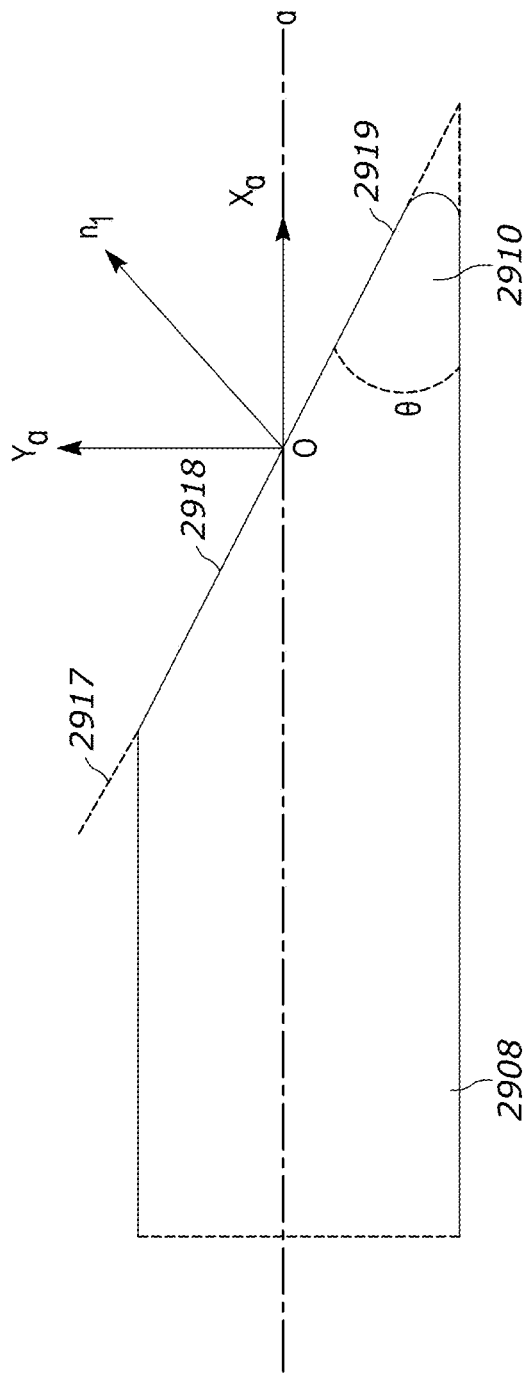
FIG. 29F illustrates a detailed view of the distal end of the tube of FIG. 29A.
Figure 29G:
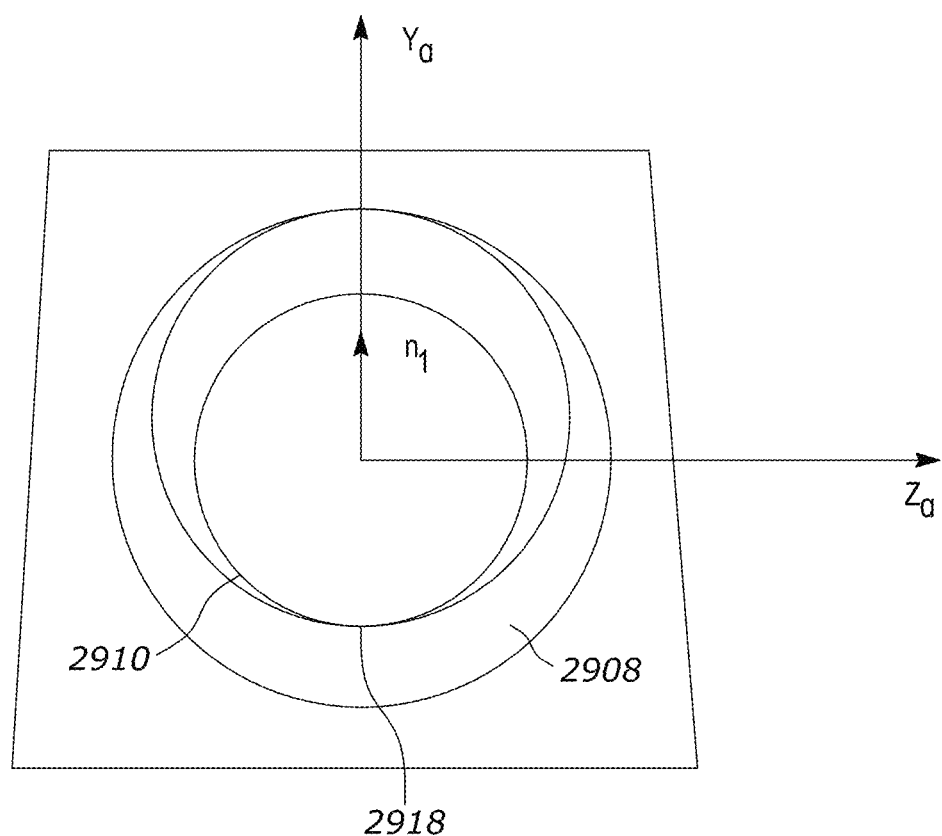
FIG. 29G illustrates an end view of the distal end of the tube of FIG. 29A.
Figure 29H:
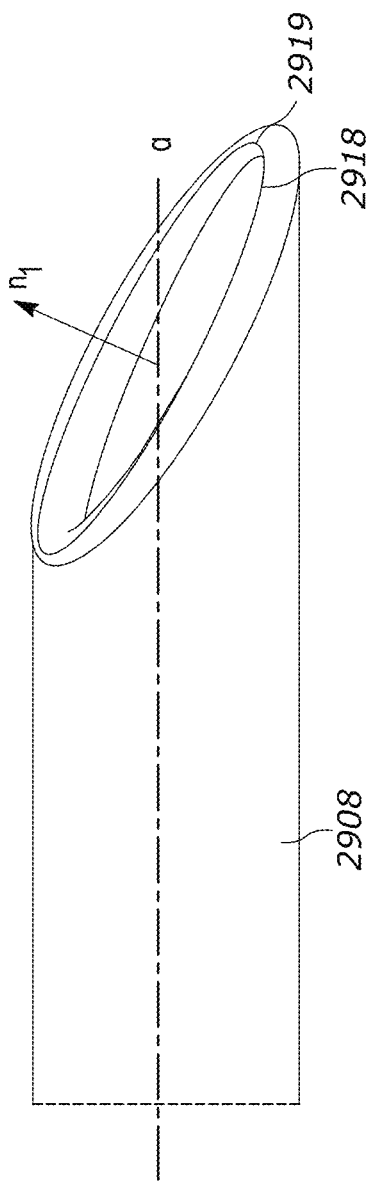
FIG. 29H illustrates another detailed view of the distal end of the tube of FIG. 29A.

Referring to FIGS. 29F, 29G, and 29H, the tube 2908 is illustrated having an opening 2918. While the tube 2908 of FIGS. 29F, 29G, and 29H are mentioned including one opening 2918 disposed at the distal end 2910, any number of openings may be defined by the tube 2908 which may be disposed in any position. Some of these alternative examples are disclosed in connection with FIGS. 29K, 30A, 30B, 30C, 42, 43, 44, 45, 48, 49, 50, 52, 53. As a further alternative, the tube 2908 may not include the opening 2918 at the distal end 2910 and, instead, may include one or more side openings such as those disclosed in connection with FIG. 36, for example. An opening center point O is defined as an intersection point between a tube center line a and a primary opening plane 2917. In the example shown, the tube 2908 has a bevel angle θ defined as the angle between a tangent of a leading edge 2919 of the opening 2918 of the tube 2908 and the primary opening plane 2917. In some examples, θ is between about 20° and about 50°. In the example shown, a reference axis $x_a$ is defined as the axis through the opening center point O, which is the tangent to the centerline a and is contiguous with the longitudinal axis of the tube 2908. A reference axis $y_a$ is defined as the axis perpendicular to $x_a$ and extends outward relative to the curvature K (see, FIG. 29B). The tube 2908 includes an inward facing surface 2905 and an outward facing surface 2907. As used herein, the phrases "outward facing surface" and "facing outward relative to the radius of curvature" refer to any surface or portion thereof that is oriented away from, or not generally oriented toward, a reference central point 2911 defined by the radius of curvature K. As an example, a direction extending outwardly relative to the radius of curvature means extending in a direction generally indicated by arrow 2909.

Referring to FIG. 29G, a reference axis $z_a$ is defined as the axis perpendicular to $x_a$ and $y_a$. In some examples, reference axes $x_a$, $y_a$, and $z_a$ are not aligned with x, y, and z given that the centerline a of the tube 2908 may be a 3D curve. The opening 2918 has a normal vector $n_1$, which is the vector perpendicular to the primary opening plane 2917. In the example shown, the normal vector $n_1$ has a component on the positive $y_a$ axis. Thus, the opening 2618 mostly faces "up" with regard to the primary curvature k allowing for the distal end 2910 of the tube 2908 to guide the tube 2908 and bend the tube 2908 away from the nasal turbinates during insertion.

Figure 29I:
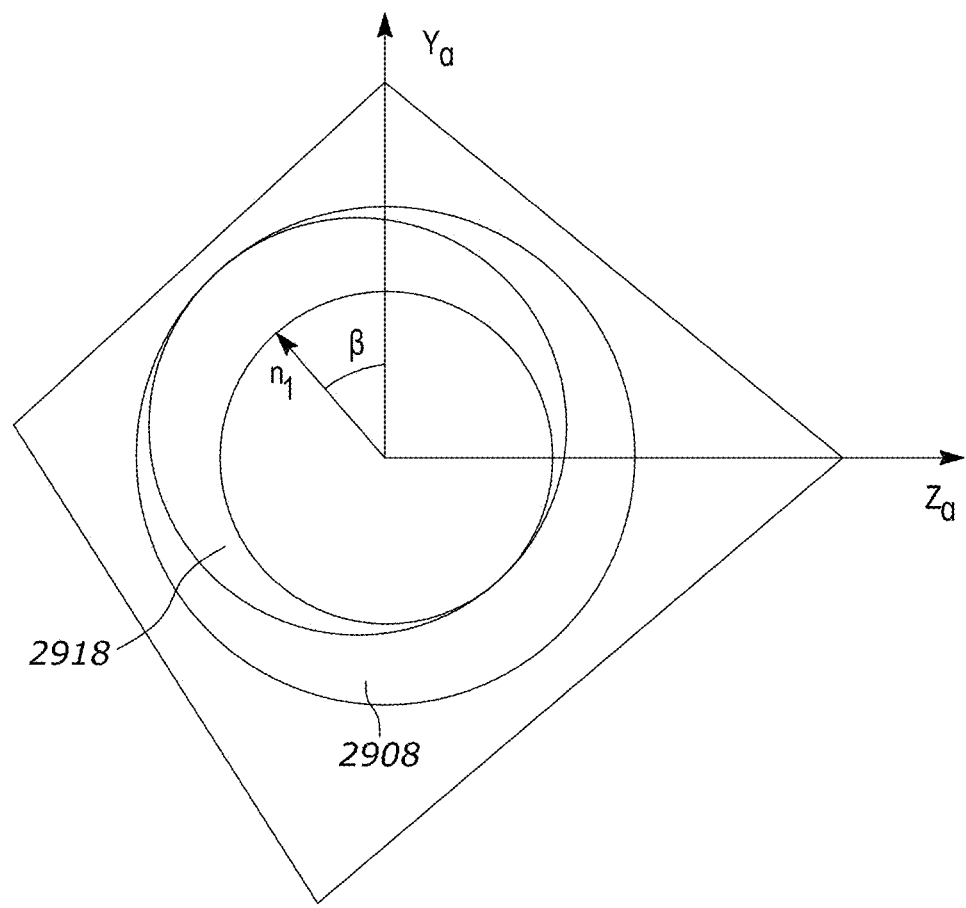
FIG. 29I illustrates a detailed view of a different distal end that may be formed on the tube of FIG. 29A.
Figure 29J:
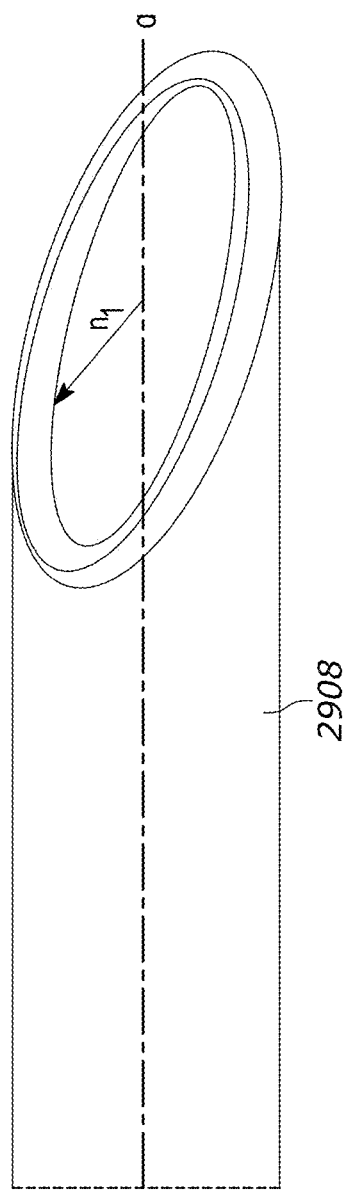
FIG. 29J illustrates another detailed view of the distal end of the tube of FIG. 29I.

Referring to FIGS. 29I and 29J, the opening 2918 is shown rotated relative to the longitudinal axis of the tube 2908. Specifically, an angle β of the normal vector $n_1$, can be between about +45° and about −45°, where the angle β is positive in the example illustrated. In some examples, a positive β angle is selected when the tube 2908 is to be inserted into a left nostril of the patient. Such a selection allows for the normal vector $n_1$ to point toward the nasal turbinates during insertion allowing for the tube 2908 to deflect away from the nasal turbinates. In some examples, a negative β angle is selected when the tube 2908 is to be inserted into a right nostril of the patient. Such a selection allows for the normal vector $n_1$ to point toward the nasal turbinates during insertion allowing for the tube 2908 to deflect away from the nasal turbinates.

Figure 29K:
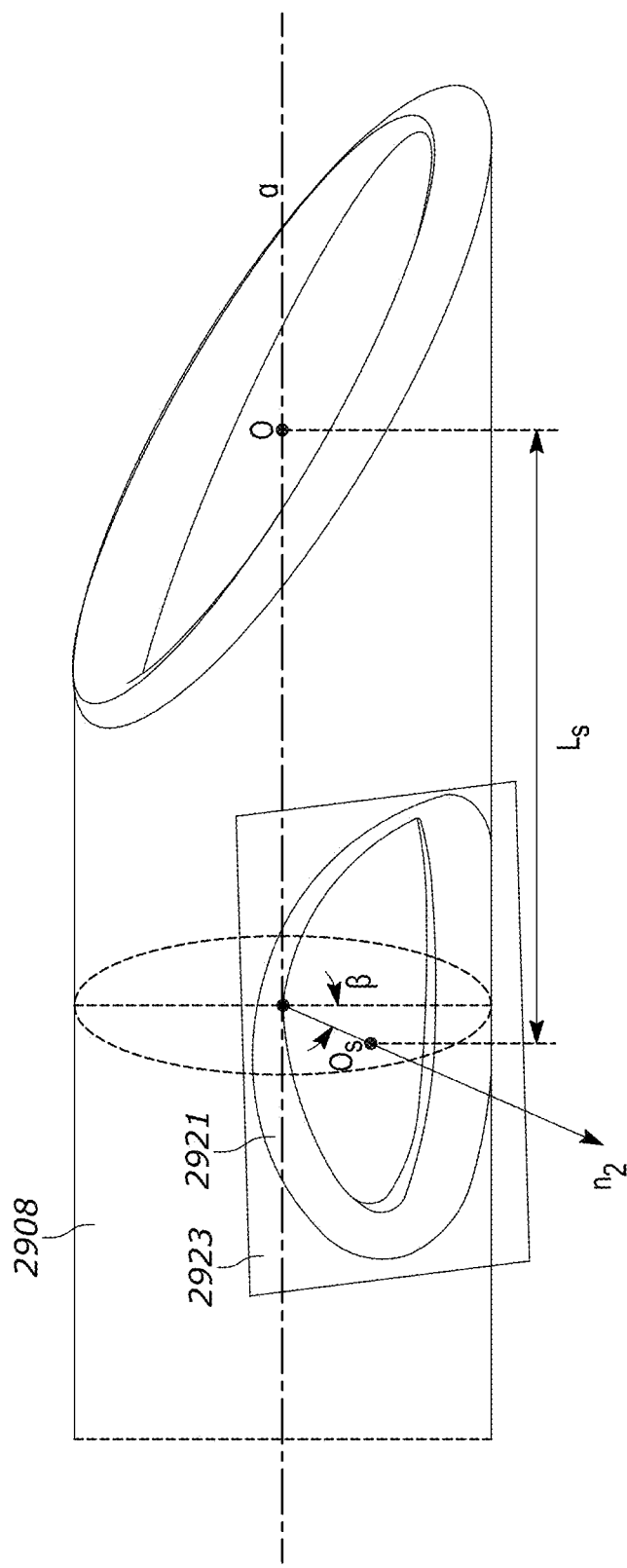
FIG. 29K illustrates a detailed view of a different distal end that may be formed on the tube of FIG. 29A including a primary opening and a secondary opening.

Referring to FIG. 29K, the tube 2908 is shown including a secondary opening 2921. While one secondary opening is shown, additional secondary openings may also be included (see, for example, FIGS. 30A, 30B and 30C). The secondary opening 2921 may be positioned enable better airway patency (e.g., ventilation openings) and/or to avoid and/or reduce mucus/liquid accumulation.

The secondary opening 2921 may have any shaped but, in the example shown, is oval shaped and includes smooth edges. If more than one secondary opening is included, each of the secondary openings may be similar to other ones of the secondary openings or each of the secondary openings may be different (e.g., a different shape, a different size, etc.). In the example shown, the secondary opening 2921 has a geometry center point $O_s$, a secondary opening plane 2923, and a normal vector $n_2$ perpendicular to the secondary opening plane 2923. The secondary opening plane 2923 is aligned with the outermost contour of the secondary opening 2921. The normal vector $n_2$ extends through the center point $O_s$, and is perpendicular to tube centerline a. The secondary opening 2921 is spaced by a length $L_s$ between the opening center point O of the opening 2918 and the center point $O_s$ of the secondary opening 2921 and is oriented relative to a radial angle β (around α). Each secondary opening can a different $L_s$ and β from the others.

Figure 30A:
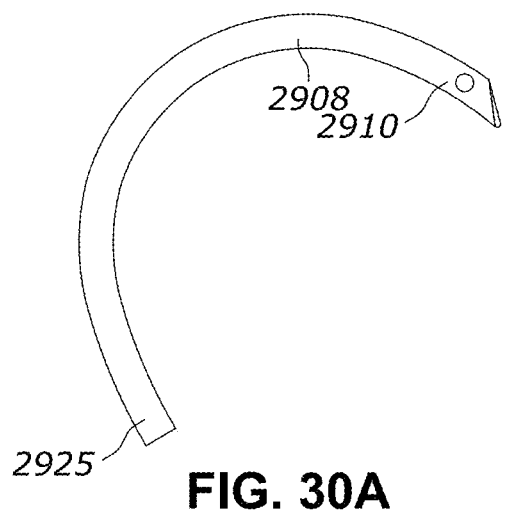
FIG. 30A illustrates the tube of FIG. 29A having a secondary opening adjacent a distal end of the tube.
Figure 30B:
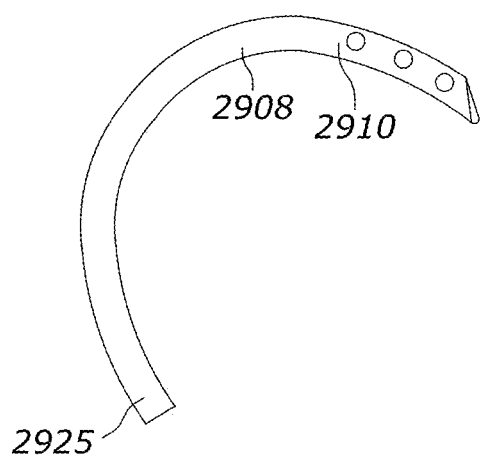
FIG. 30B illustrates the tube of FIG. 29A having a plurality of secondary openings adjacent a distal end of the tube.
Figure 30C:
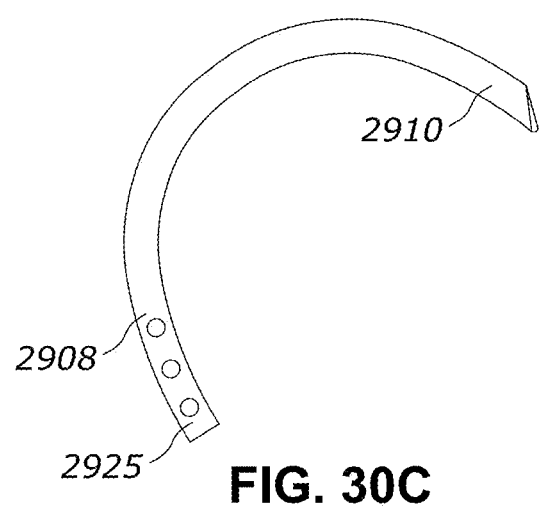
FIG. 30C illustrates the tube of FIG. 29A having a plurality of secondary openings adjacent a proximal end of the tube.

FIGS. 30A, 30B and 30C illustrate that the secondary openings 2921 can be positioned nearby the distal end 2910 of the tube 2908, nearby a proximal end 2925 of the tube 2908, or throughout the tube 2908.

Figure 31A:
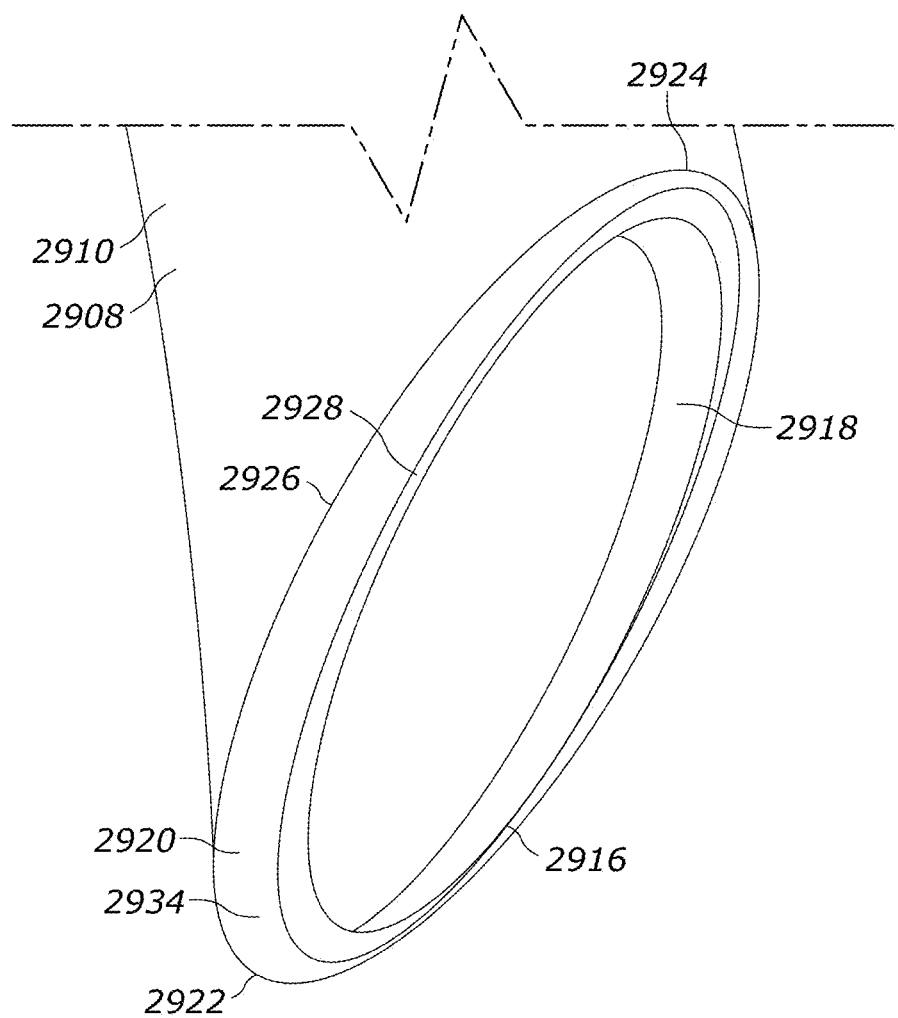
FIG. 31A illustrates a detailed view of the distal end of the tube of FIG. 29A.

FIG. 31A illustrates a detailed view of the distal end 2910 of the tube 2908. In the example shown, an end surface 2916 at the distal end 2110 includes the opening 2918 that is defined by a fillet 2920. While the fillet 2920 is shown in FIG. 31A, other configurations have been contemplated to allow the distal end 2910 of the tube 2908 to be, for example, smooth and/or rounded. As an example, the fillet 2920 may alternatively be formed as a bevel. That fillet 2920 may surround the opening 2918. In an example, the fillet 2920 is relatively short. When the opening 2918 is non-perpendicular relative to a plane that bisects an axis of the tube 2908, the opening 2918 may be oblong or may otherwise have a non-circular shape. Additionally or alternatively, the opening 2918 may be formed as an annulus (e.g., an oblong-shaped annulus).

Figure 31B:
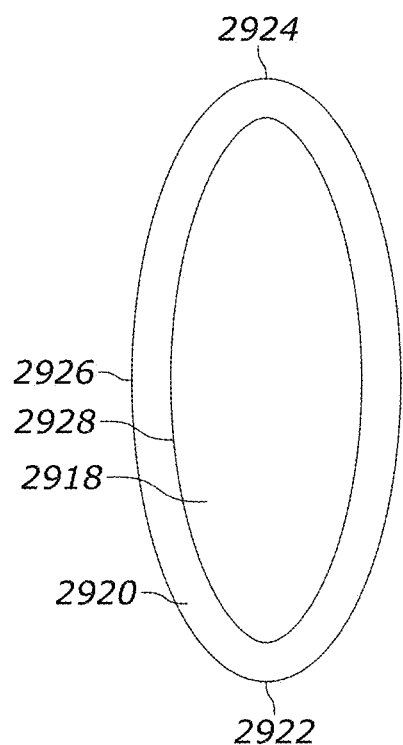
FIG. 31B illustrates a schematic perspective illustration of an opening and an annulus of the tube of FIG. 29A.

FIG. 31B illustrates a schematic perspective illustration of the opening 2918 and the fillet 2920. The fillet 2920 includes a leading end (leading edge) 2922, a trailing end (trailing edge) 2924, an outer portion 2926 and an inner portion 2928.

Referring back to FIG. 31A, in the example shown, the end surface 2916 includes a convex surface 2934 that includes the leading end 2922. The convex surface 2934 is atraumatic and, thus, may assist in guiding and/or bending the tube 2908 when the tube 2908 is inserted into the nostril 2902 and the nasal cavity 2904. The convex surface 2934 may allow the leading end 2922 to be fed into the nostril 2902 and the nasal cavity 2904 with the opening 2918 facing a top of the patient's 2906 head (See, FIG. 29), while also reducing discomfort and tissue injury.

Figure 32:
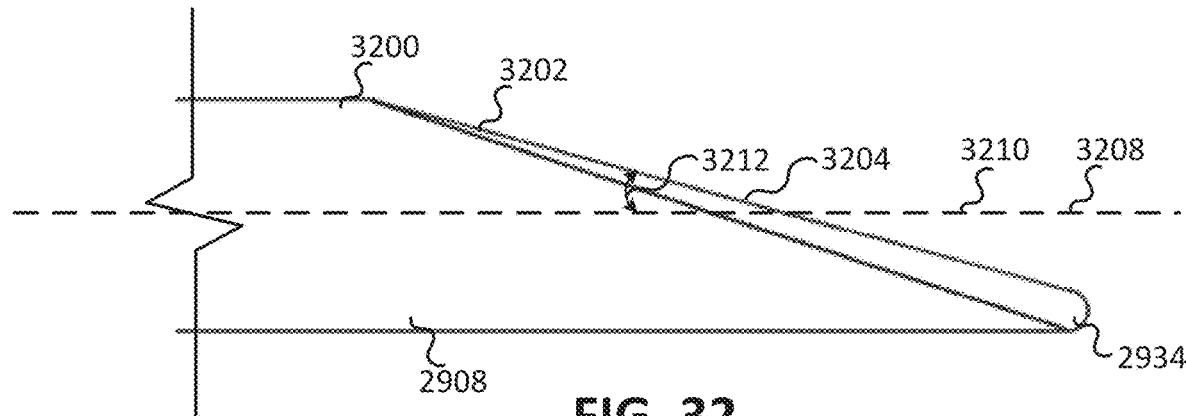
FIG. 32 illustrates a different distal end that may be formed on the tube of FIG. 29A.
Figure 33:
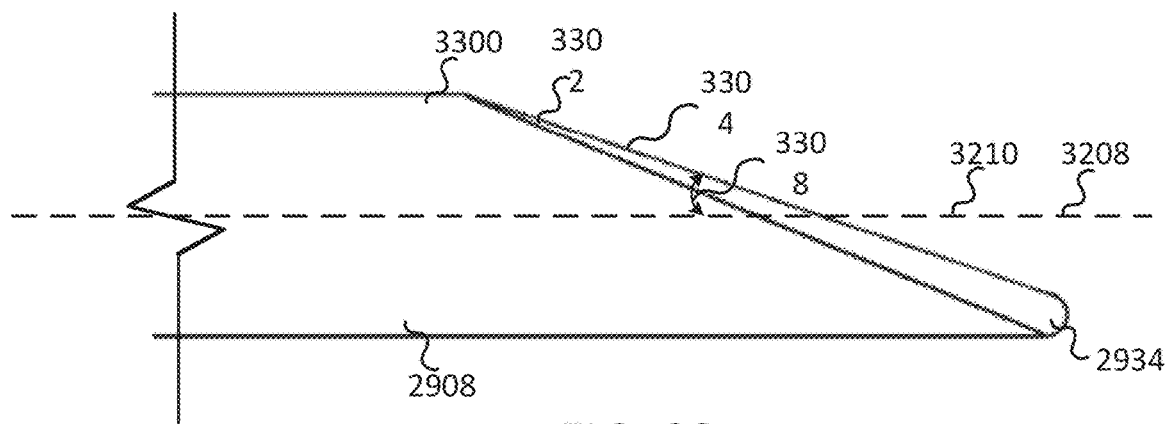
FIG. 33 illustrates another distal end that may be formed on the tube of FIG. 29A.
Figure 34:
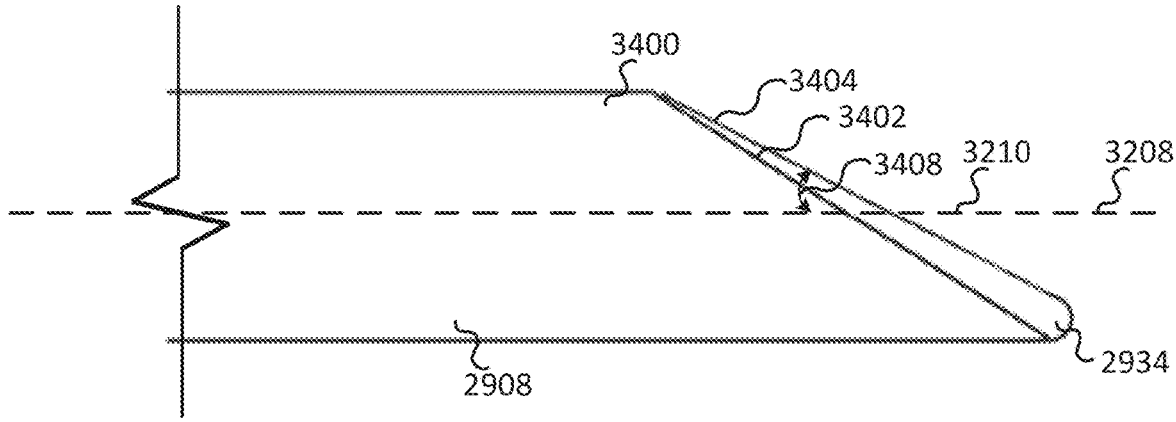
FIG. 34 illustrates another distal end that may be formed on the tube of FIG. 29A.

FIGS. 32-34 illustrate different distal ends 3200, 3300, 3400 that may be formed on the tube 2908 in accordance with the teachings of the present disclosure. The distal ends 3200, 3300, 3400 are similar to one another but include annuluses 3202, 3302, 3402 and associated inner portions 3204, 3304, 3404 that have different angles relative to a reference plane 3208. The reference plane 3208 is shown bisecting an axis 3210 of the tube 2908.

In the examples shown, an angle 3212 of the inner portion 3204 of the annulus 3202 of FIG. 32 is approximately 15° relative to the plane 3208; an angle 3308 of the inner portion 3304 of the annulus 3302 of FIG. 33 is approximately 18° relative to the plane 3208; and an angle 3408 of the inner portion 3404 of the annulus 3402 of FIG. 34 is approximately 27° relative to the plane 3208. While the inner portions 3204, 3304, 3404 are shown having specific angles, generally, the angles 3212, 3308, 3408 may be different (e.g., 22°, 27°, 30°, 35°, 45°, etc.). More generally, in some examples, the angle is between about 30° and about 50°.

Figure 35:
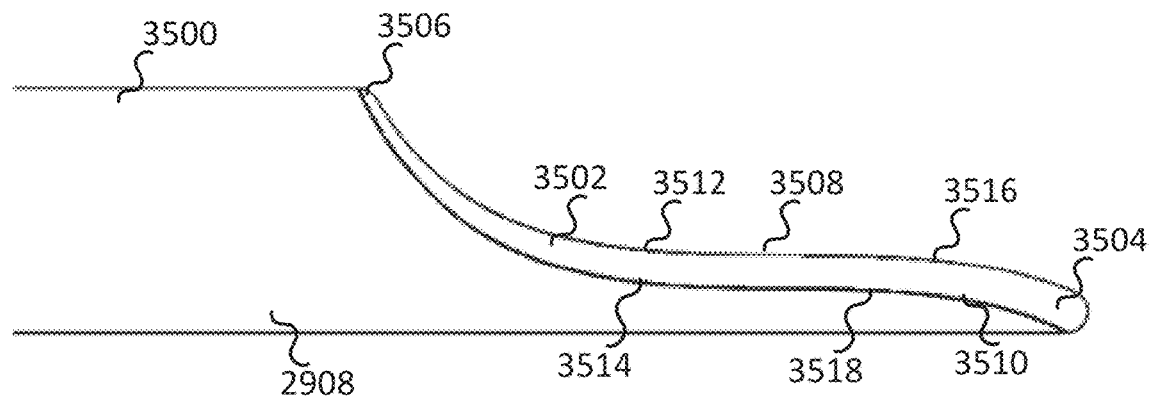
FIG. 35 illustrates another distal end that may be formed on the tube of FIG. 29A.

FIG. 35 illustrates another distal end 3500 that may be formed on the tube 2908 in accordance with the teachings of the present disclosure. The distal end 3500 includes an annulus 3502 having a leading end 3504 and a trailing end 3506 and defining an opening (not shown). In contrast to the examples above, the annulus 3502 includes sides 3508, 3510 that are curvilinear and include concave portions 3512, 3514 and convex portions 3516, 3518 with respect to the nasal cavity. In the example shown, the concave portions 3512, 3514 are positioned closer to the trailing end 3506 and the convex portions 3516, 3518 are positioned closer to the leading end 3504. While the annulus 3502 itself is shown having one concave portion and one convex portion, the annulus 3402 may alternatively include any number of concave portions (e.g., 0, 2, etc.) and any number of convex portions (e.g., 0, 2, etc.).

Figure 36:
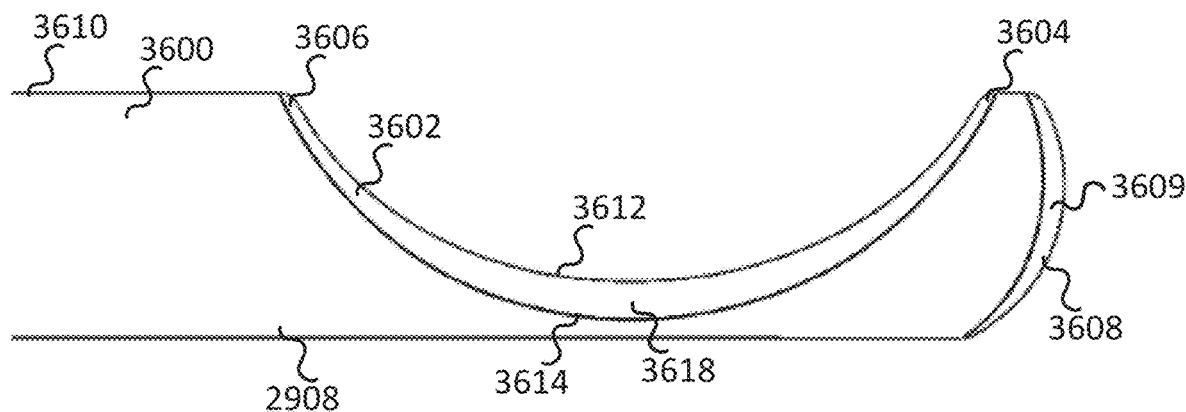
FIG. 36 illustrates another distal end that may be formed on the tube of FIG. 29A.

FIG. 36 illustrates another distal end 3600 that may be formed on the tube 2908 in accordance with the teachings of the present disclosure. The distal end 3600 includes an annulus 3602 having a leading end 3604 and a trailing end 3606 and defining an opening (not shown). In contrast to the examples disclosed above, the distal end 3600 includes a closed end 3608 and the opening is formed in a side 3610 of the tube 2908. In the example shown, a plane that bisects the apex 2913 of the tube 2908 and the axis 3210 of the tube 2908 also substantially bisects the leading end 3604 and the trailing end 3606 of the opening. As set forth herein, substantially bisecting the leading end 3604 and the trailing end 3606 means +/−5°. In the orientation of the tube 2908 shown in FIG. 36, the plane is vertical and extends from the left to the right.

The leading end 3604 of the annulus 3602 is spaced from the closed end 3608. The closed end 3608 is rounded and may include one or more convex portions 3609. The rounded nature of the closed end 3608 may reduce discomfort and tissue injury when the tube 2908 is inserted into the nostril 2902 and the nasal cavity 2904. The annulus 3602 includes an inner portion 3612, an outer portion 3614 and a central portion 3618. The central portion 3618 is disposed between the trailing end 3606 and the leading end 3604. Put another way, the opening faces upward.

FIGS. 37-39 illustrate the tube 2908 having different radiuses of curvature and including inward-facing surfaces 3702 and outward-facing surfaces 3704. The distal ends disclosed above may be formed on any one of the tubes 2908 of FIGS. 37-39. While not shown in FIGS. 37-39, in some examples, the inward-facing surfaces 3702 terminate at the leading end of the respective annuluses and the outward-facing surfaces 3704 terminate at the trailing end of the respective annuluses.

Figure 40:
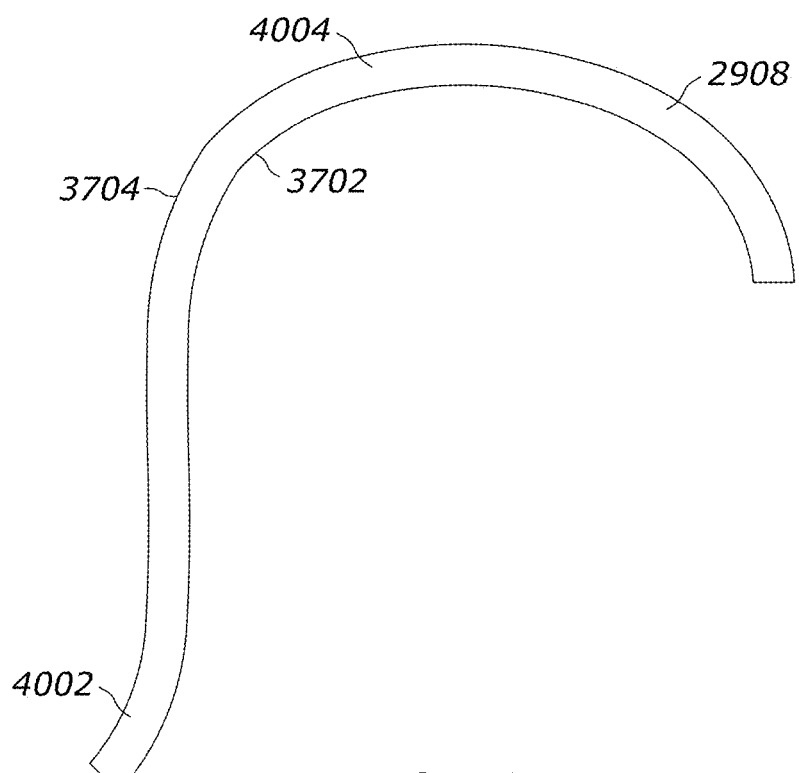
FIG. 40 illustrates the tube of FIG. 29A having a concave portion and a convex portion.
Figure 41:
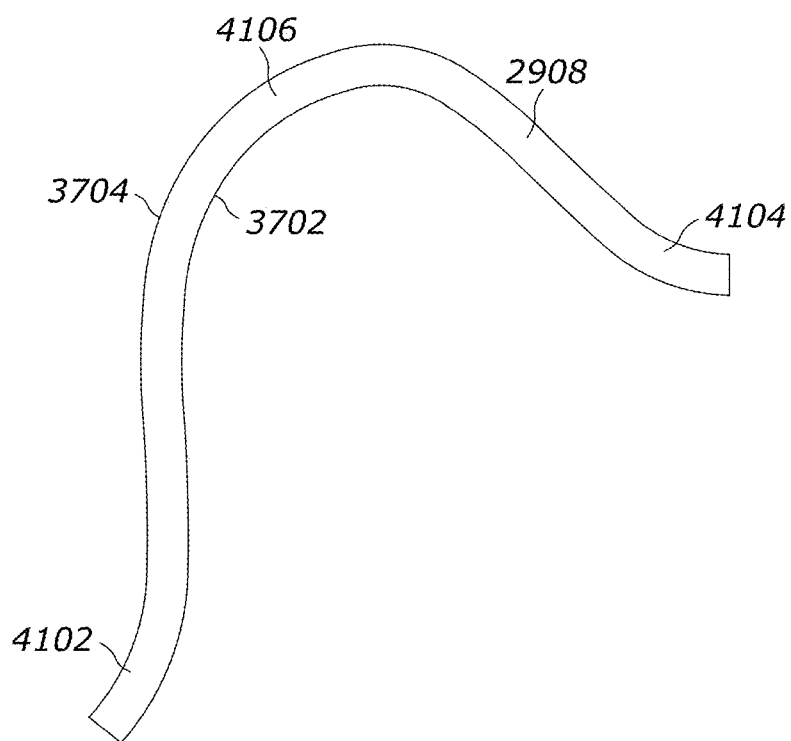
FIG. 41 illustrates the tube of FIG. 29A having concave portions and a convex portion.

FIGS. 40 and 41 illustrate the tube 2908 having a tube centerline with at least one curvature forming a primary curvature (overall curvature) that forms an overall curvature with a radius of curvature relative to the tube centerline. In the examples shown in FIGS. 40 and 41, the tube 2908 includes concave portions 4002, 4102, 4104 and convex portions 4004, 4106 relative to the tube centerline (the axis) of the tube 2908. The distal ends disclosed above may be formed on any one of the tubes 2908 of FIGS. 40-41. While the tube 2908 is shown in FIGS. 40-41 having a particular shape, the tube 2908 may have any number of convex portions and any number of concave portions (including zero) between the ends of the tube 2908. Put another way, the curvature of the tube 2908 may take any form that makes insertion into the nostril 2902 and the nasal cavity 2904 easier.

Figure 42:
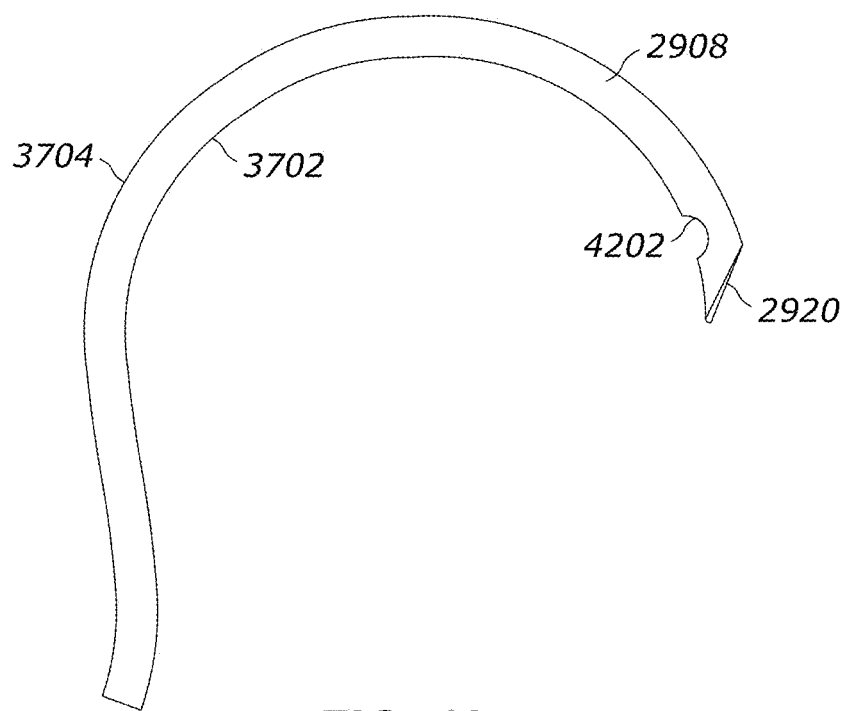
FIG. 42 illustrates the tube of FIG. 29A having an inward-facing surface that defines a side opening.

FIG. 42 illustrates the tube 2908 including the inward-facing surface 3702 that defines a side opening 4202. The side opening 4202 may have an arc-shaped cross-section (as shown) or another cross-section such, as, for example, a rectangular cross-section (See, FIG. 45).

Figure 43:
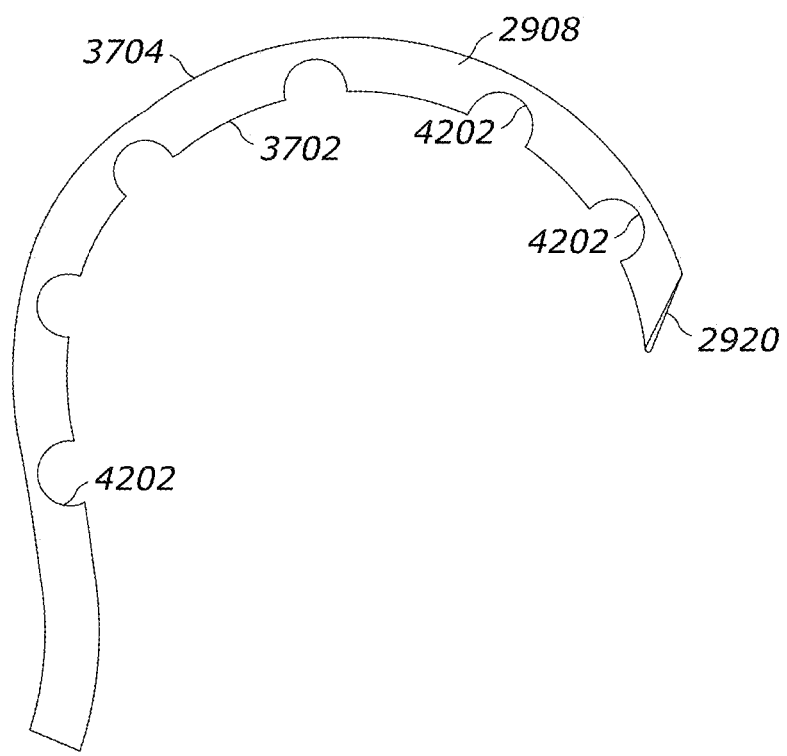
FIG. 43 illustrates the tube of FIG. 29A having a plurality of the side openings.

FIG. 43 illustrates the tube 2908 having a plurality of the side openings 4202 (e.g., perforations). The placement of the side openings 4202 may encourage the tube 2908 to bend as the tube 2908 is inserted into the nostril 2902 and the nasal cavity 2904 and may provide the tube 2908 with a threshold amount of rigidity (e.g., variable opening geometry).

Figure 44:
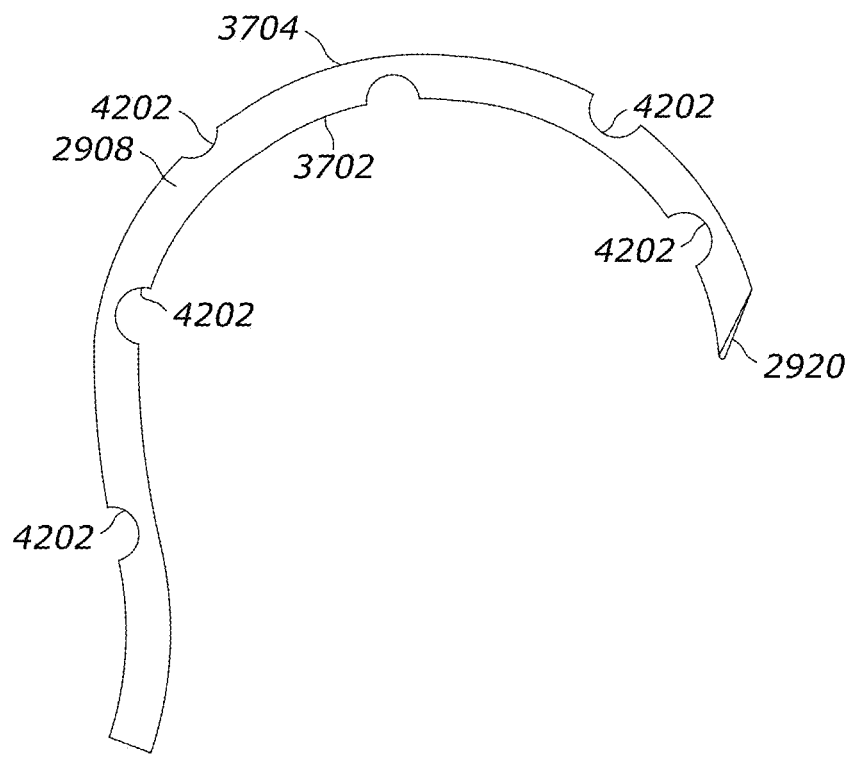
FIG. 44 illustrates the tube of FIG. 29A having a plurality of side openings on an inward-facing surface and on an outward-facing surface.

FIG. 44 illustrates the tube 2908 having the plurality of side openings 4202 on the inward-facing surface 3702 and the outward-facing surface 3704. In the example shown, the side openings 4202 on the inward-facing surface 3702 are positioned between the side openings 4202 on the outward-facing surface 3704.

Figure 45:
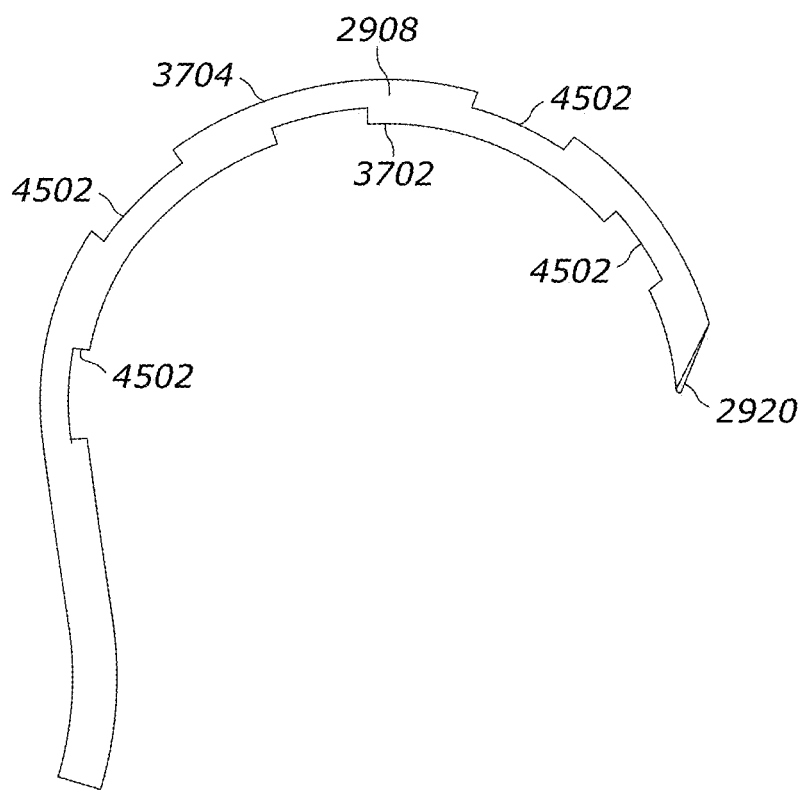
FIG. 45 illustrates the tube of FIG. 29A having a plurality of side openings on the inward-facing surface and the outward-facing surface, where the side openings of FIG. 45 have a different cross-section than the side openings formed on the tube of FIG. 44.

FIG. 45 illustrates the tube 2908 having a plurality of side openings 4502 on the inward-facing surface 3702 and the outward-facing surface 3704. The side openings 4502 are similar to the side openings 4202 of FIGS. 42-49, but the side openings 4502 of FIG. 45 have a rectangular cross-section. The side openings 4202 and/or 4502 may be located to increase airway patency and/or deter nasal mucus/liquid accumulation. In some examples, the tube 2908 of any of the disclosed examples includes a hydrophobic coating on an interior surface of the tube 2908 and/or an exterior surface of the tube 2908. The hydrophobic coating may be adapted to deter nasal mucus/liquid accumulation.

Figure 46A:
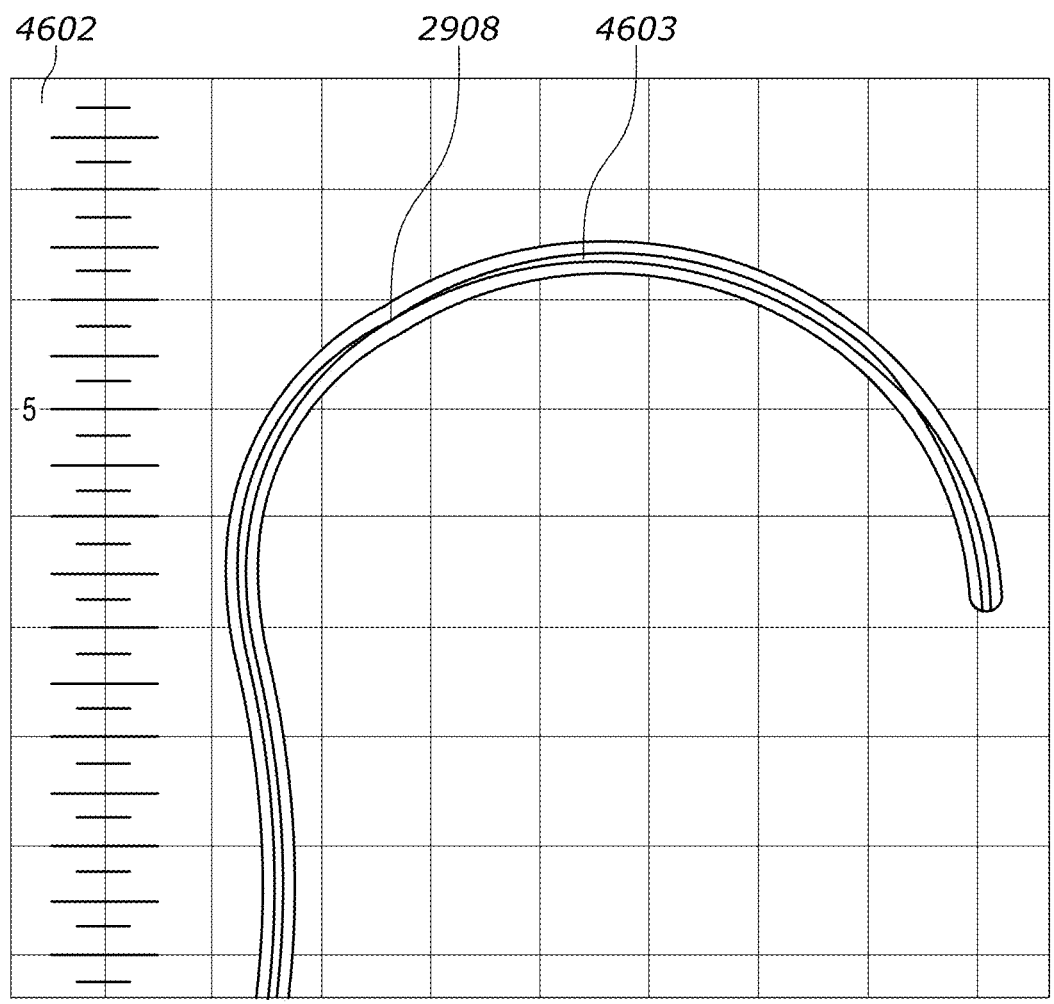
FIG. 46A illustrates the tube of FIG. 29A positioned on a grid showing a radius curvature of the tube.

FIG. 46A illustrates the tube 2908 positioned on a grid 4602 showing the radius of curvature of the tube 2908. The grid 4602 includes markings in half inches. Thus, in the example shown, the radius of curvature is about 1.75 inches. In the example shown, the tube 2908 has at least one curvature throughout a body 4603 of the tube 2908 which forms an overall curvature with the radius of curvature relative to a longitudinal axis of the tube.

Figure 46B:
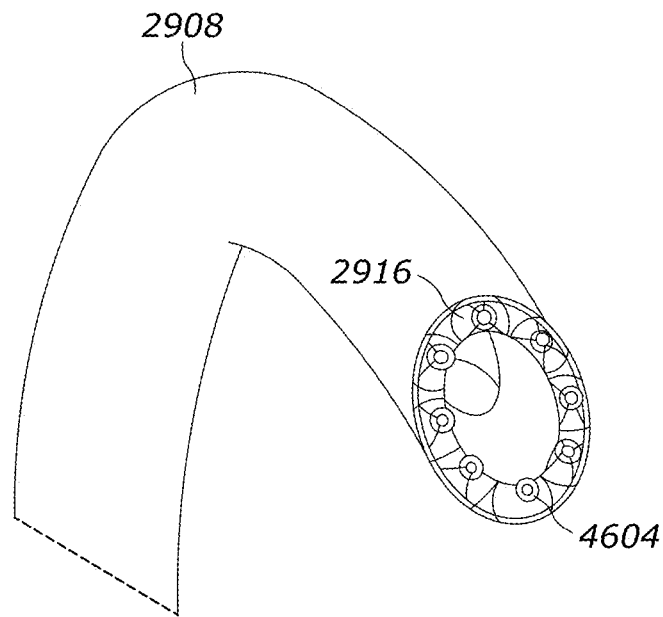
FIG. 46B illustrates the end surface of the tube of FIG. 29A including protrusions.
Figure 46C:
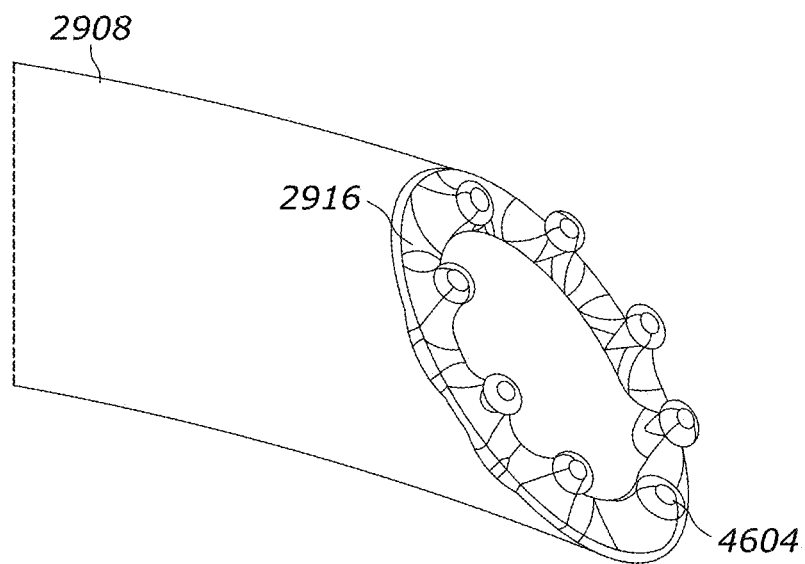
FIG. 46C illustrates a detailed view of the tube of FIG. 46B.

FIGS. 46B and 46C illustrate the end surface 2916 including protrusions 4604. The protrusions 4604 are configured to decrease surface tension of mucus/liquid nearby the tube 2908 and avoid and/or reduce the accumulation of mucus/liquid inside the tube 2908. In some examples, a coating (e.g. hydrophobic material) or surface texture can be applied on the interior/exterior surface of tube 2908 to avoid and/or reduce mucus/liquid clogging inside the tube 2908.

Figure 47:
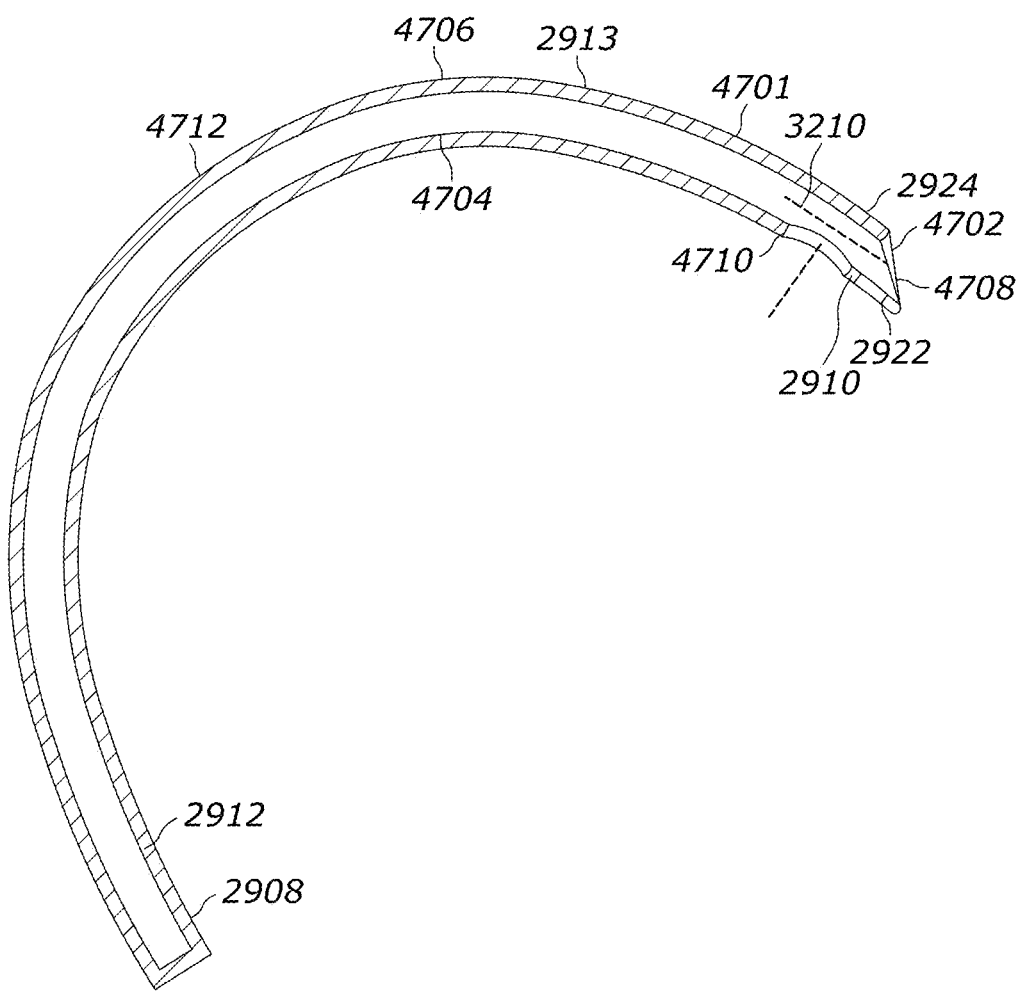
FIG. 47 illustrates a cross-sectional view of the tube of FIG. 29A including a first opening and a secondary opening.

FIG. 47 illustrates the tube 2908 having another distal end 4701 in accordance with the teachings of this disclosure. The tube 2908 of FIG. 47 has a radius of curvature of between about 0.030 mm$^{-1}$ and 0.017 mm$^{-1}$ or between about 0.010- about 0.04 mm$^{-1}$. Such a radius of curvature may follow a medial line of the head of the patient 2906. Providing such a radius of curvature may, in some examples, assist in guiding the tube 2908 away from turbinates of the nose when the tube 2908 is being inserted into the nostril 2902 and/or the nasal cavity 2904. In the illustrated example of FIG. 47, the tube 2908 has a length of between about 8 cm and about 15 cm, an outer diameter of between about 4 mm and about 6 mm and a wall thickness of between about 0.5 mm and about 1.0 mm.

The tube 2908 includes an end surface 4702, a lower surface 4704 and an upper surface 4706. The end surface 4702 defines a first opening 4708. The leading end 2922 may be rounded to remove edges that may cause irritation and/tissue damage when the tube 2908 is being inserted into the nostril 2902.

In the example shown, the leading end 2922 is the lowest-most point of the first opening 4708 and the trailing end 2924 is the highest most point of the first opening 4708. Thus, the leading end 2922 is spaced a maximum and/or greater distance from the apex 2913 of the tube 2908 when, for example, the tube 2908 is being inserted into the nostril 2902 of the patient 2906 (see, FIG. 29).

The lower surface 4704 of the tube 2908 also defines a second opening (a lateral opening) 4710. The second opening 4710 may be referred to as a murphy eye and, in the example shown, has an oval shape and includes smooth and/or rounded edges. While one of murphy eye is illustrated in FIG. 47 adjacent the distal end 2910 of the tube 2908, additional murphy eyes may be included and/or the second opening 4710 may be defined in a different location. For example, the tube 2908 may define one or more murphy eyes adjacent the distal end 4701 of the tube 2908, a central portion 4712 of the tube 2908 and/or adjacent the proximal end 2912 of the tube 2908. The murphy eyes may be spaced at different distances from the distal end 2910 and at different locations around the tube 2908 relative to the axis 3210 of the tube 2908. One or more of the lateral openings can be similar or different from one or more others of the lateral openings. Such lateral openings may improve airway patency and/or deter mucus accumulation.

Figure 48:
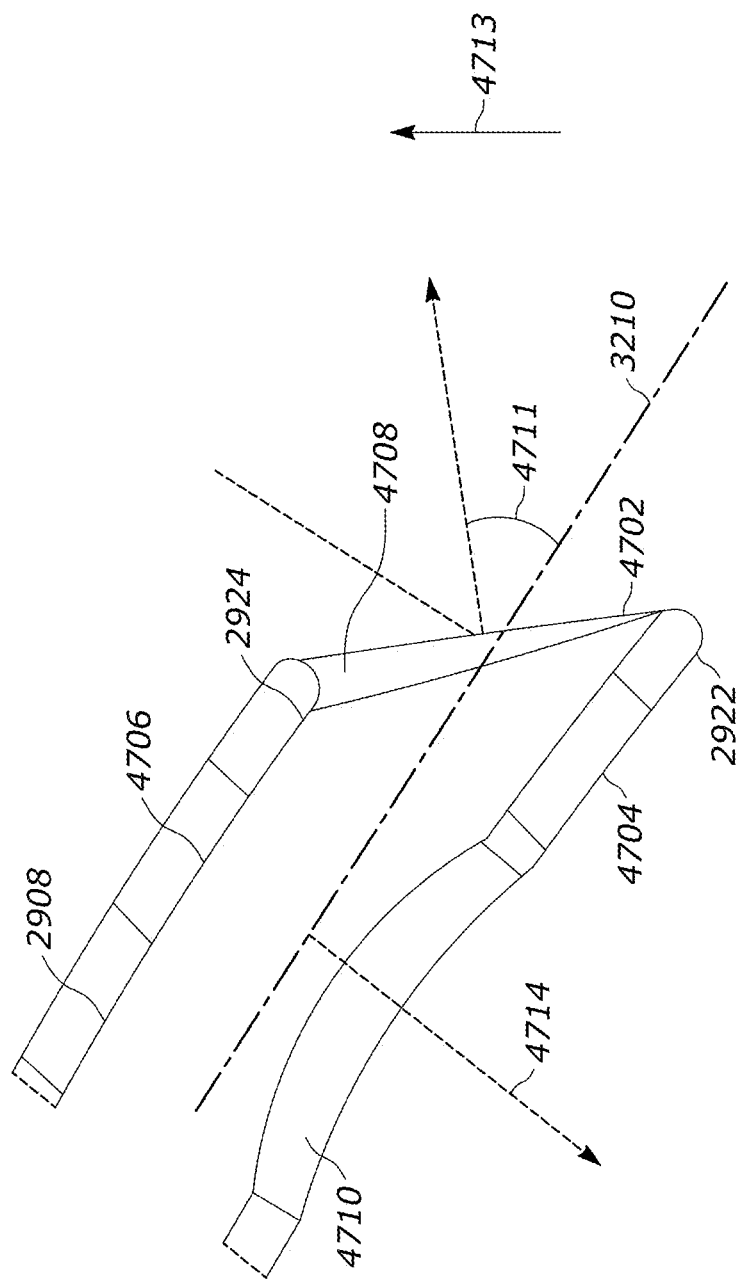
FIG. 48 illustrates a detailed view of the tube of FIG. 47.

FIG. 48 illustrates a detailed view of the end surface 4702, the first opening 4708 and the second opening 4710. The lower surface 4704 of the tube 2908 ends at the leading end 2922 of the first opening 4708 and the upper surface 4706 of the tube 2908 ends at the trailing end 2924 of the first opening 4708. In the example shown, an angle 4711 of the end surface 4702 relative to the reference plane 3208 (see, FIGS. 32-34) is between about 30° and about 50°. Thus, the first opening 4708 opens in a direction generally indicated by arrow 4713 and upward relative a direction that the tube 2908 is curving. Additionally, in the example shown, an axis 4714 of the second opening 4710 is illustrated being substantially perpendicular to the plane 3208 and, thus, the axis 3210 of the tube 2908. If the location of the second opening 4710 is differently positioned, the axis 4714 may be normal to a plane defined at an exterior surface of the tube 2908, for example.

Figure 49:
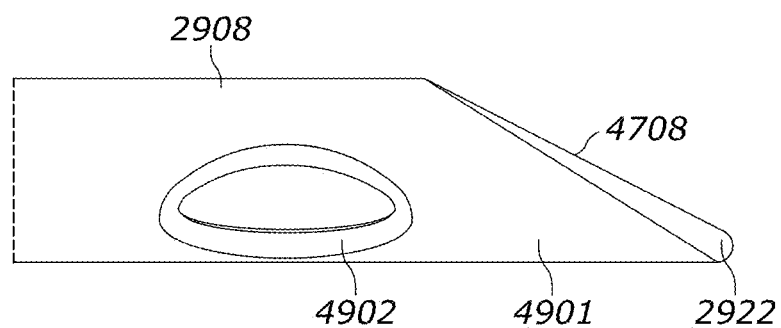
FIG. 49 illustrates a different distal end formed on the tube of the FIG. 29A including first and second side openings.
Figure 50:
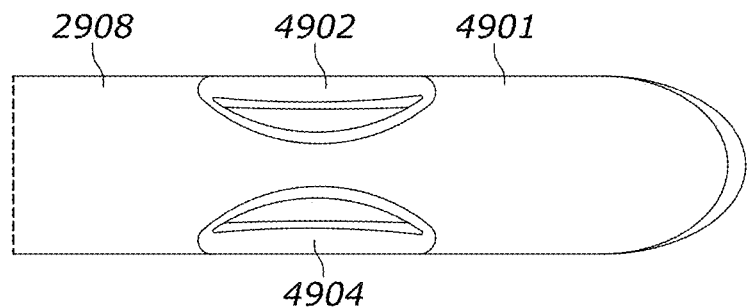
FIG. 50 illustrates another view of the tube of FIG. 49 more clearly showing the first and second openings.

FIGS. 49-53 illustrate the tube 2908 having the one or more lateral openings positioned in different locations. FIGS. 49 and 50 illustrate different views of the tube 2908 having a distal end 4901 including first and second side openings 4902, 4904. In the example shown, the openings 4902, 4904 have a length of about 5 mm and about 7 mm and are spaced from each other around the axis 3210 at approximately +/-60°. Also, the first and second openings 4902, 4904 are equally spaced from a leading end 2922 of the first opening 4708.

Figure 51:
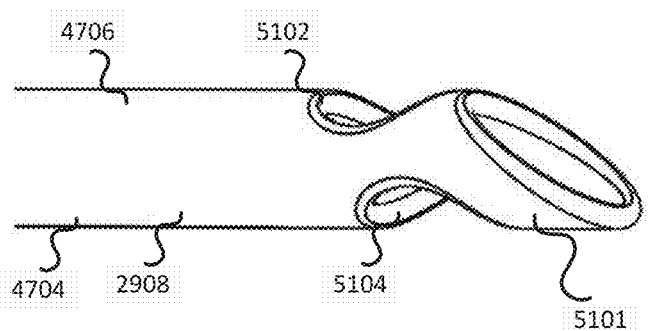
FIG. 51 illustrates a different distal end formed on the tube of FIG. 29A having first and second openings, where the first opening is defined by an upper surface of the tube and the second opening is defined by a lower surface of the tube.

FIG. 51 illustrates another view of the tube 2908 having another distal end 5101 including first and second openings 5102, 5104. In contrast to the tube 2908 shown in FIGS. 49 and 50, the first opening 5102 is defined by the upper surface 4706 of the tube 2908 and the second opening 5104 is defined by the lower surface 4704 of the tube 2908.

Figure 52:
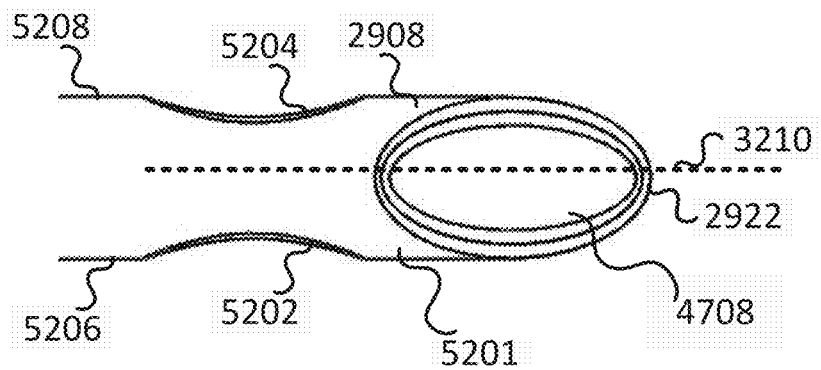
FIG. 52 illustrates a different distal end formed on the tube of FIG. 29A having first and second openings defined by side surfaces of the tube.

FIG. 52 illustrates the tube 2908 having another distal end 5201 including first and second opening 5202, 5204 defined by side surfaces 5206, 5208 of the tube 2908. The openings 5202, 5204 are equally spaced from the leading end 2922 of the first opening 4708 and are spaced about the axis 3210 of the tube 2908.

Figure 53:
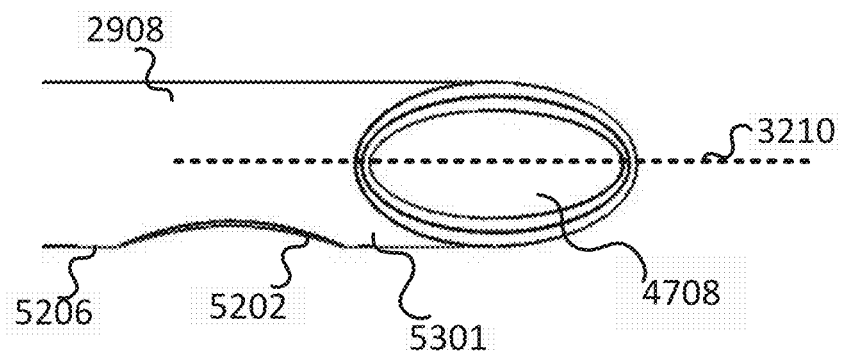
FIG. 53 illustrates a view of the tube of FIG. 29A having one opening defined by one of the side surfaces of the tube.

FIG. 53 illustrates another view of the tube 2908 having another distal end 5301 including the opening 5202 defined by the side surface 5206 but not including the opening 5204.

Figure 54:
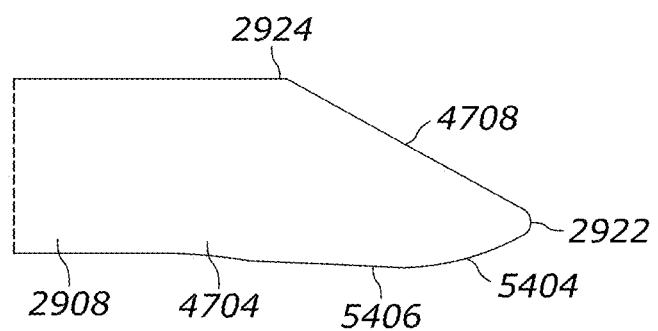
FIG. 54 illustrates a different distal end formed on the tube having a protrusion formed on a lower surface of the tube.

FIG. 54 illustrates a side view of the tube 2908 including a distal end 5404 including a protrusion 5406. The protrusion 5406 is formed on the lower surface 4704 of the tube 2908. The protrusion 5406 is adapted to further round the distal end 5404 of the tube 2908 to allow the tube 2908 to be more easily inserted into the nostril 2902. In the example shown, the protrusion 5406 is a transition point (e.g., a corner) of the tube 2908 and has an oval shape. The protrusion 5406 is spaced from the leading end 2922 of the openings 4708.

As used in this specification and the appended claims, the singular forms "a", "an", and "the" include plural references unless the context clearly dictates otherwise.

As used herein, a nasal tube of the airway device encompasses any tube or tube-like structure entering one or both nostrils. This can include, but is not limited to, nasopharyngeal, nasotracheal, and nasogastric tubes.

While specific embodiments have been described herein, variations may be made to the described embodiments that are still considered within the scope of the appended claims.

What is claimed is:

1. A nasal airway device comprising:
   a tube having a distal end and a proximal end; and
   an attachment mechanism coupled to the proximal end of the tube, the attachment mechanism including:
      a sliding member having a tubular shape having a top annular surface and a bottom annular surface, and an exterior circular side surface that extends between the top annular surface to the bottom annular surface;
      a tube access channel comprising a top annular surface, a bottom surface, an exterior circular side surface that extends between the top annular surface of the tube access channel and the bottom surface of the tube access channel;
      a plurality of fins on the exterior circular side surface of the tube access channel and each having a first end and a second end, at least one of the plurality of fins being deformable, the fins connected to the exterior circular side surface of the sliding member at the first ends and to the exterior circular side surface of the tube access channel at the second ends, wherein the top annular surface of the tube access channel faces the bottom annular surface of the sliding member, and wherein the entire top annular surface of the tube access channel is spaced from the entire bottom annular surface of the sliding member such that the sliding member is supported on the tubular access channel by only the plurality of fins; and
      a bridge connected at a proximal portion of the exterior surface of the tube access channel,
   wherein the sliding member is configured to slide relative to the tube to change a relative distance between the sliding member annular surface and the tube access channel annular surface to adjust a width of the fins, and
   wherein the plurality of fins and the sliding member are configured to be inserted into a nostril of a patient.

2. The nasal airway device of claim 1, wherein the tube comprises:
   a tubular body having the distal end and the proximal end, wherein a surface at the distal end includes an opening,
   the tubular body having an overall curvature with a radius of curvature defined relative to a longitudinal axis of the tube,
   wherein an X-axis is defined by the longitudinal axis of the tube, and a Y-axis extends perpendicularly from the longitudinal axis and has a positive direction defined outwardly relative to the radius of curvature,
   wherein at least a portion of the opening faces outwardly relative to the radius of curvature, and
   wherein a vector normal to a plane defined by the opening includes a positive Y-coordinate.

3. The nasal airway device of claim 2, wherein the opening includes a leading end and a trailing end, the leading end being closest, relative to the trailing end, to a lowest most point of the opening and the trailing end being closest, relative to the leading end, to a highest most point of the opening, the leading end being spaced a greater distance from an apex of the tube than the trailing end when the tube is being inserted into the nostril of the patient.

4. The nasal airway device of claim 2, wherein the opening includes a leading end and a trailing end, and wherein a first plane bisects an apex of the tube and the leading end and the trailing end of the opening.

5. The nasal airway device of claim 2, wherein the opening includes a leading end and a trailing end, and wherein a first plane bisects an apex of the tube and a second plane bisects the leading end and the trailing end, an angle defined between the first plane and the second plane is between about 0° and about 45°.

6. The nasal airway device of claim 2, wherein an angle between the vector and the Y-axis is between about 0° and about positive 45° to adapt the nasal airway tube to be inserted into the nostril of the patient.

7. The nasal airway device of claim 2, further comprising a side opening defined by the tube.

8. The nasal airway device of claim 2, wherein the tube has a radius of curvature of between about 0.010 millimeters $(mm)^{-1}$ and about 0.04 $mm^{-1}$.

9. The nasal airway device of claim 2, wherein a lower surface of the tube adjacent the opening includes a protrusion.

10. The nasal airway device of claim 2, wherein along an axis of the tube between a trailing end and a leading end of the opening, respective sides of the opening include associated convex portions and associated concave portions.

11. The nasal airway device of claim 2, wherein the opening includes a leading end and a trailing end and the tube includes an outward-facing surface and an inward-facing surface, the outward-facing surface terminating at the trailing end and the inward-facing surface terminating at the leading end.

12. The nasal airway device of claim 1, wherein the fins are semi-occluding.

13. The nasal airway device of claim 12,
   wherein the fins are spaced around a circumference of the exterior circular side surface of the tube access channel by one or more angles, or
   wherein at least one of the fins includes a cutout.

14. The nasal airway device of claim 1, wherein the fins include at least one of an adhesive to improve securement and surface texture.

15. The nasal airway device of claim 1, wherein the bridge includes a hook that curves or projects toward a distal end of the attachment mechanism.

16. The nasal airway device of claim 1, wherein the tube access channel is a first tube access channel, and wherein the bridge connects the first tube access channel to a second tube access channel.

17. The nasal airway device of claim 1, wherein the sliding member surrounds the tube.

18. An attachment mechanism for a nasal airway device, comprising:
- a tube access channel comprises a top annular surface, a bottom surface, and an exterior circular side surface extending between the top annular surface and the bottom surface;
- a sliding member comprising a tubular shape having a top annular surface and a bottom annular surface, and an exterior circular surface that extends from the top annular surface of the sliding member to the bottom annular surface of the sliding member; and
- a plurality of fins, wherein the plurality of fins and the sliding member are configured to be inserted into a nostril of a patient and the sliding member is configured to receive a tube of the nasal airway device, each of the plurality of fins comprises a first end and a second end, the first end of each of the plurality of fins extends from the exterior circular surface of the sliding member and the second end of each of the plurality of fins extends from the exterior circular side surface of the tube access channel, wherein the top annular surface of the tube access channel faces the bottom annular surface of the sliding member, wherein the entire top annular surface of the tube access channel is spaced from the entire bottom annular surface of the sliding member such that the sliding member is supported on the tubular access channel by only the plurality of fins.

* * * * *